(12) United States Patent
Chen et al.

(10) Patent No.: US 11,865,234 B2
(45) Date of Patent: Jan. 9, 2024

(54) TREATMENT APPARATUS FOR A VEHICLE TO TREAT AN OBJECT WITH ULTRAVIOLET LIGHT

(71) Applicant: Ford Global Technologies, LLC, Dearborn, MI (US)

(72) Inventors: Jay Z. Chen, Sylvania, OH (US); Anthony Ligi, Jr., Chelsea, MI (US); John Robert Van Wiemeersch, Novi, MI (US); Michael Hrecznyj, Livonia, MI (US); Clay Wesley Maranville, Ypsilanti, MI (US); Amy Ellen Langhorst, Ann Arbor, MI (US); Rick H. Wykoff, Commerce Township, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 853 days.

(21) Appl. No.: 16/837,653

(22) Filed: Apr. 1, 2020

(65) Prior Publication Data
US 2021/0308317 A1 Oct. 7, 2021

(51) Int. Cl.
*A61L 9/20* (2006.01)
*A61L 2/10* (2006.01)
*B60H 3/06* (2006.01)

(52) U.S. Cl.
CPC .............. *A61L 9/20* (2013.01); *A61L 2/10* (2013.01); *B60H 3/06* (2013.01); *A61L 2202/14* (2013.01); *A61L 2202/16* (2013.01)

(58) Field of Classification Search
CPC .......... A61L 9/20; A61L 2/10; A61L 2202/14; A61L 2202/16
See application file for complete search history.

(56) References Cited

U.S. PATENT DOCUMENTS

| | | | |
|---|---|---|---|
| 6,908,597 B2 | 6/2005 | Chen et al. | |
| 9,592,312 B2 | 3/2017 | Lyslo et al. | |
| 10,376,605 B1 | 8/2019 | Majdali et al. | |
| 2002/0098109 A1 | 7/2002 | Nelson et al. | |
| 2007/0053188 A1 | 3/2007 | New et al. | |
| 2007/0207066 A1 | 9/2007 | Thur et al. | |
| 2008/0175761 A1 | 7/2008 | Thur et al. | |
| 2008/0265179 A1* | 10/2008 | Havens | A61L 2/10 250/492.1 |
| 2010/0237649 A1 | 9/2010 | Concina | |

(Continued)

FOREIGN PATENT DOCUMENTS

| | | |
|---|---|---|
| CN | 2726973 Y | 9/2005 |
| DE | 102016215247 A1 | 2/2018 |

(Continued)

*Primary Examiner* — Sean E Conley
(74) *Attorney, Agent, or Firm* — Vichit Chea; Price Heneveld LLP

(57) ABSTRACT

A treatment apparatus for a vehicle comprises: a housing with at least one wall and a floor forming a treatment chamber; a source of ultraviolet light configured to emit ultraviolet light into the treatment chamber; and a door connected to the housing, the door having (i) an open position providing access to the treatment chamber and (ii) a closed position denying access to the treatment chamber and, together with the housing, preventing emitted ultraviolet light from irradiating beyond the treatment chamber.

19 Claims, 16 Drawing Sheets

(56) References Cited

U.S. PATENT DOCUMENTS

| | | | |
|---|---|---|---|
| 2010/0266445 A1* | 10/2010 | Campagna | A61L 2/202 422/23 |
| 2012/0144569 A1* | 6/2012 | Kodat | A47K 13/302 4/222 |
| 2014/0245866 A1* | 9/2014 | Hadlock | A61L 2/10 81/9.2 |
| 2016/0000951 A1 | 1/2016 | Kreiner et al. | |
| 2016/0089459 A1 | 3/2016 | Boodaghians et al. | |
| 2016/0250362 A1 | 9/2016 | Mackin | |
| 2017/0313278 A1 | 11/2017 | Marew | |
| 2018/0065126 A1 | 3/2018 | Abate et al. | |
| 2019/0076558 A1 | 3/2019 | Zhang-Miske | |
| 2020/0101183 A1* | 4/2020 | Dijkstra | A61L 2/28 |

FOREIGN PATENT DOCUMENTS

| | | | |
|---|---|---|---|
| DE | 102018002328 A1 | 9/2019 | |
| EP | 2668964 A1 | 12/2013 | |
| EP | 26678964 A1 | 12/2013 | |
| JP | 2005130994 A | 5/2005 | |
| JP | 2011073617 A | 4/2011 | |
| KR | 0124687 Y1 | 6/1998 | |
| WO | WO 2018126034 | * | 7/2018 |

* cited by examiner

TREATMENT APPARATUS FOR A VEHICLE TO TREAT AN OBJECT WITH ULTRAVIOLET LIGHT

FIELD OF THE DISCLOSURE

The present disclosure generally relates to a treatment apparatus for a vehicle to treat an object inserted into the treatment apparatus with ultraviolet light, in order to reduce the amount of pathogens on the object.

BACKGROUND OF THE DISCLOSURE

A surface can transmit pathogens to a person. A person sometimes handles an object with surfaces containing pathogens. A vehicle used for ride-hailing or ride-sharing sometimes encounters such people and objects.

Ultraviolet light can inactivate pathogens. However, implementing ultraviolet light to disinfect an object in the vehicle poses a variety of problems. A first problem is that emitted ultraviolet light could cause a plastic component of an interior of the vehicle to degrade and become more brittle in a process referred to as photo-oxidation. A second problem is that emitting ultraviolet light could degrade the apparatus used for emitting the ultraviolet light, either through photo-oxidation of a plastic component of the apparatus or through thermal degradation of the source of ultraviolet light. A third problem is that emitting ultraviolet light after the ultraviolet light has disinfected the object (i.e., killed or inactivated a significant portion of the pathogens) wastes energy and increases the chances of a realization of the first and second problems.

SUMMARY OF THE DISCLOSURE

According to one aspect of the present invention, a treatment apparatus for a vehicle comprises: a housing with at least one wall and a floor forming a treatment chamber; a source of ultraviolet light configured to emit ultraviolet light into the treatment chamber; and a door connected to the housing, the door having (i) an open position providing access to the treatment chamber and (ii) a closed position denying access to the treatment chamber and, together with the housing, preventing emitted ultraviolet light from irradiating beyond the treatment chamber.

Embodiments of the first aspect of the invention can include any one or a combination of the following features:
- the source of ultraviolet light does not emit ultraviolet light if the door is in the open position;
- the treatment apparatus further comprises a sensor that produces output that varies as a function of the door being in the open position or the closed position;
- the treatment apparatus further comprises a controller in communication with the sensor and the source of ultraviolet light, the controller deactivates the source of ultraviolet light when the sensor produces output indicative of the door being in the open position;
- the treatment apparatus further comprises a bandpass filter disposed between the source of ultraviolet light and the treatment chamber that transmits less than 10 percent of ultraviolet light having a wavelength of 290 nm to 400 nm but transmits greater than 10 percent of ultraviolet light having a wavelength of 240 nm to 280 nm;
- the treatment apparatus further comprises a display;
- the controller is further in communication with the display, and the controller causes the display to provide a visual indication that the source of ultraviolet light is emitting ultraviolet light when the controller is causing the source of ultraviolet light to emit ultraviolet light;
- the treatment apparatus is disposed within the vehicle at one or more of a center console, a second center console, an overhead console, or a dashboard; and
- the treatment apparatus further includes a locking system that prevents the door from transitioning from the closed position to the open position while the source of ultraviolet light is emitting ultraviolet light.

According to a second aspect of the present invention, a treatment apparatus for a vehicle comprises: a housing with a wall and a floor forming a treatment chamber; a source of ultraviolet light configured to emit ultraviolet light into the treatment chamber; and either (i) a bandpass filter disposed between the source of ultraviolet light and the treatment chamber that transmits less than 10 percent of ultraviolet light having a wavelength of 290 nm to 400 nm but greater than 10 percent of ultraviolet light having a wavelength of 240 nm to 280 nm, (ii) a metal heatsink in thermal communication with the source of ultraviolet light, (iii) a fan positioned to circulate air onto the source of ultraviolet light or a printed circuit board upon which the source of ultraviolet light is mounted; or (iv) a sensor in communication with a controller, the sensor producing output to the controller that varies as a function of a temperature of the source of ultraviolet light or a printed circuit board upon which the source of ultraviolet light is mounted, and the controller deactivates the source of ultraviolet light as a function of the output of the sensor.

Embodiments of the second aspect of the invention can include any one or a combination of the following features:
- the treatment apparatus further comprises a coating disposed over a portion of the housing open to the treatment chamber that reflects at least 50 percent of ultraviolet light having a wavelength of 240 nm to 280 nm;
- the treatment apparatus further comprises a door connected to the housing, the door having (i) an open position providing access to the treatment chamber and (ii) a closed position denying access to the treatment chamber;
- the coating is further disposed over a portion of the door that is open to the treatment chamber;
- the treatment apparatus further comprises the metal heatsink in thermal communication with the source of ultraviolet light;
- the treatment apparatus further comprises the fan positioned to circulate air onto the source of ultraviolet light or the printed circuit board upon which the source of ultraviolet light is mounted; and
- the treatment apparatus further comprises the sensor in communication with the controller, the sensor producing output to the controller that varies as a function of the temperature of the source of ultraviolet light or the printed circuit board upon which the source of ultraviolet light is mounted generates, and the controller deactivates the source of ultraviolet light as a function of the output of the sensor.

According to a third aspect of the present invention, a treatment apparatus for a vehicle comprises: a housing with at least one wall and a floor forming a treatment chamber; a source of ultraviolet light configured to emit ultraviolet light into the treatment chamber; and a controller in communication with the source of ultraviolet light that causes the source of ultraviolet light to emit ultraviolet light for a predetermined period of time and, upon conclusion of the predetermined period of time, deactivates the source of ultraviolet light.

Embodiments of the third aspect of the invention can include any one or a combination of the following features:

the treatment apparatus further comprises a user interface in communication with the controller where a passenger of the vehicle inputs the predetermined period of time that the source of ultraviolet light is to emit ultraviolet light into the treatment chamber;

the controller causes the source of ultraviolet light to emit ultraviolet light for the predetermined period of time and, upon conclusion of the predetermined period of time, deactivates the source of ultraviolet light;

the controller determines (i) a total energy that the source of ultraviolet light is to emit into the treatment chamber, and (ii) an intensity of ultraviolet light as a function of the total energy and the predetermined period of time;

the controller causes the source of ultraviolet light to emit ultraviolet light for the predetermined period of time and at the intensity, and, upon conclusion of the predetermined period of time, deactivates the source of ultraviolet light;

the treatment apparatus further comprises a user interface in communication with the controller, the user interface providing selectable options for identifying an object to be treated in the treatment chamber for a passenger of the vehicle to select as a selected option of the selectable options;

the controller determines the predetermined period of time as a function of the selected option, and causes the source of ultraviolet light to emit ultraviolet light for the predetermined period of time, and, upon conclusion of the predetermined period of time, deactivates the source of ultraviolet light;

the treatment apparatus further comprises a camera in communication with the controller that captures an image of an object to be treated in the treatment chamber;

the controller determines the predetermined period of time as a function of the image of the object, causes the source of ultraviolet light to emit ultraviolet light for the predetermined period of time, and, upon conclusion of the predetermined period of time, deactivates the source of ultraviolet light;

the treatment apparatus further comprises a sensor in communication with the controller that collects a volume of airborne particulate matter and provides a signal to the controller that varies as a function of the volume of airborne particulate matter collected;

the controller activates the source of ultraviolet light as a function of the signal from the sensor, causes the source of ultraviolet light to emit ultraviolet light for the predetermined period of time, and deactivates the source of ultraviolet light;

the sensor comprises an adhesion layer where the volume of airborne particulate matter is collected, a light source directing light to a first side of the adhesion layer, and a photodetector disposed on a second side of the adhesion layer;

the photodetector provides output that varies as a function of the volume of airborne particulate matter collected at the adhesion layer; and a first airflow to a junction causes a second airflow from the treatment chamber to flow to the junction and combine into combined airflow, and the combined airflow of the first airflow and the second airflow directs the volume of airborne particulate matter to a collection chamber that includes the adhesion layer.

These and other aspects, objects, and features of the present invention will be understood and appreciated by those skilled in the art upon studying the following specification, claims, and appended drawings.

DETAILED DESCRIPTION OF THE PREFERRED EMBODIMENTS

Figure 1:
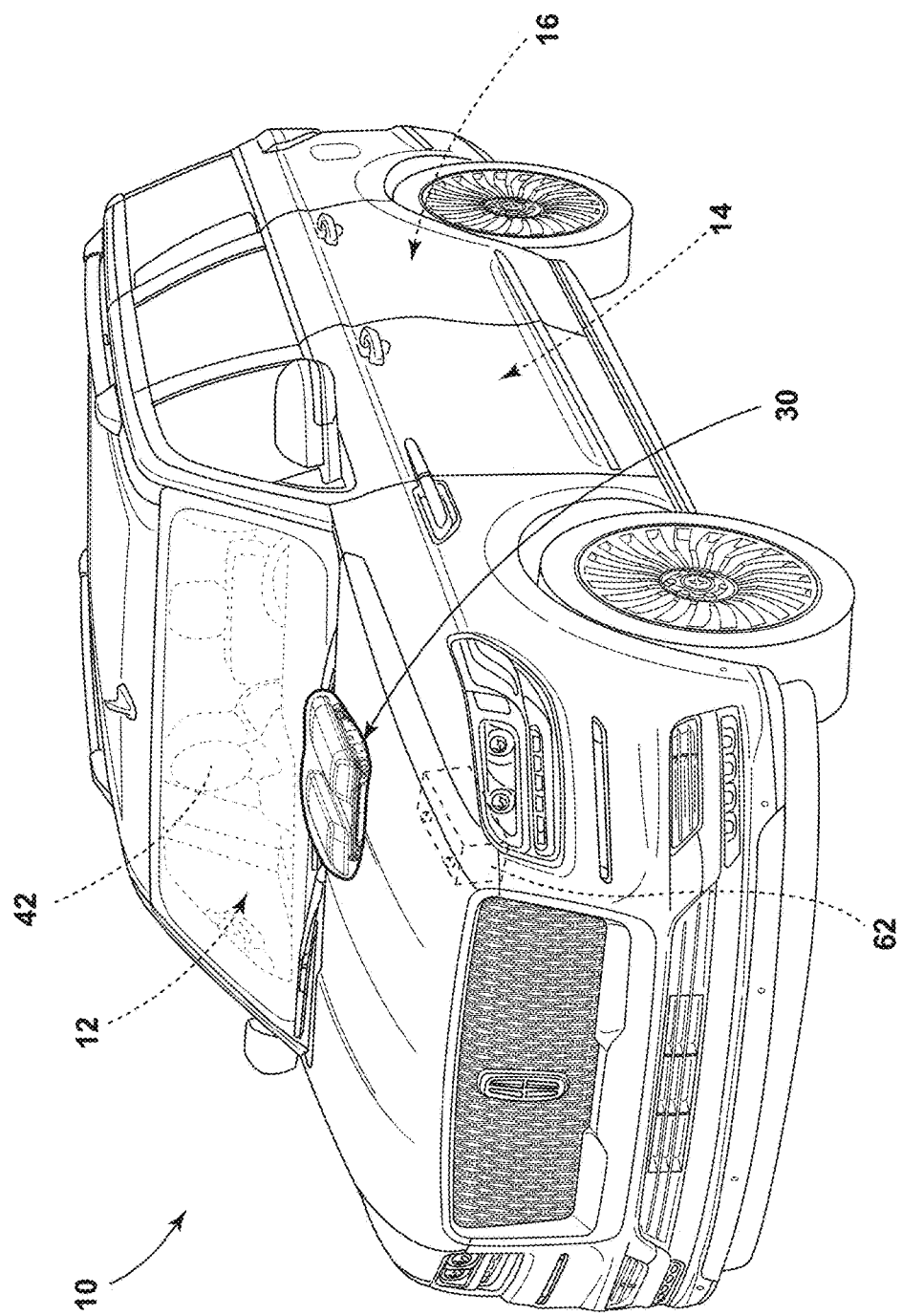
FIG. 1 is a perspective view of a front of a vehicle, illustrating a treatment apparatus within an interior of the vehicle.
Figure 2:
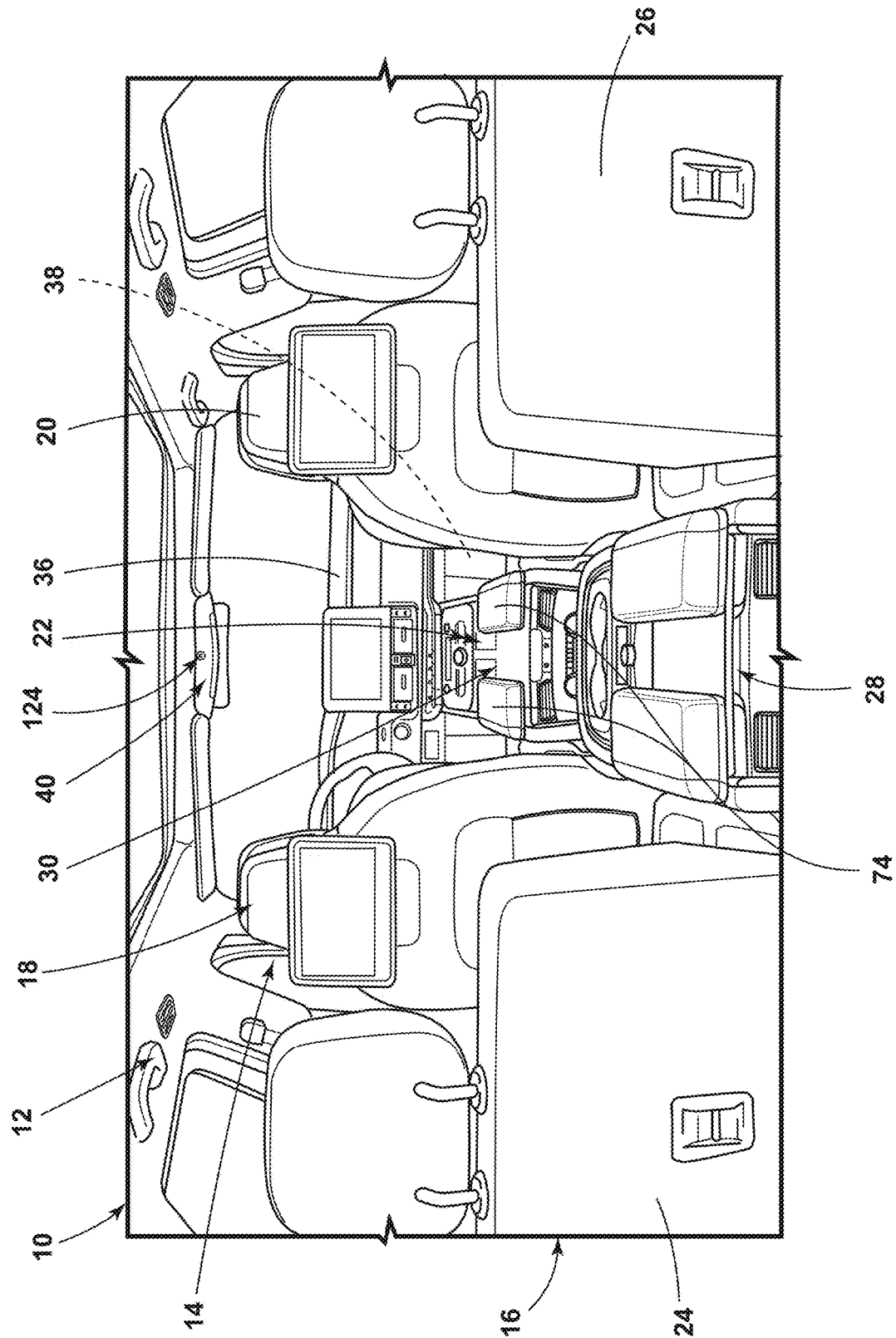
FIG. 2 is a perspective view looking forward within the interior of the vehicle, illustrating the treatment apparatus disposed between two seating assemblies.
Figure 3:
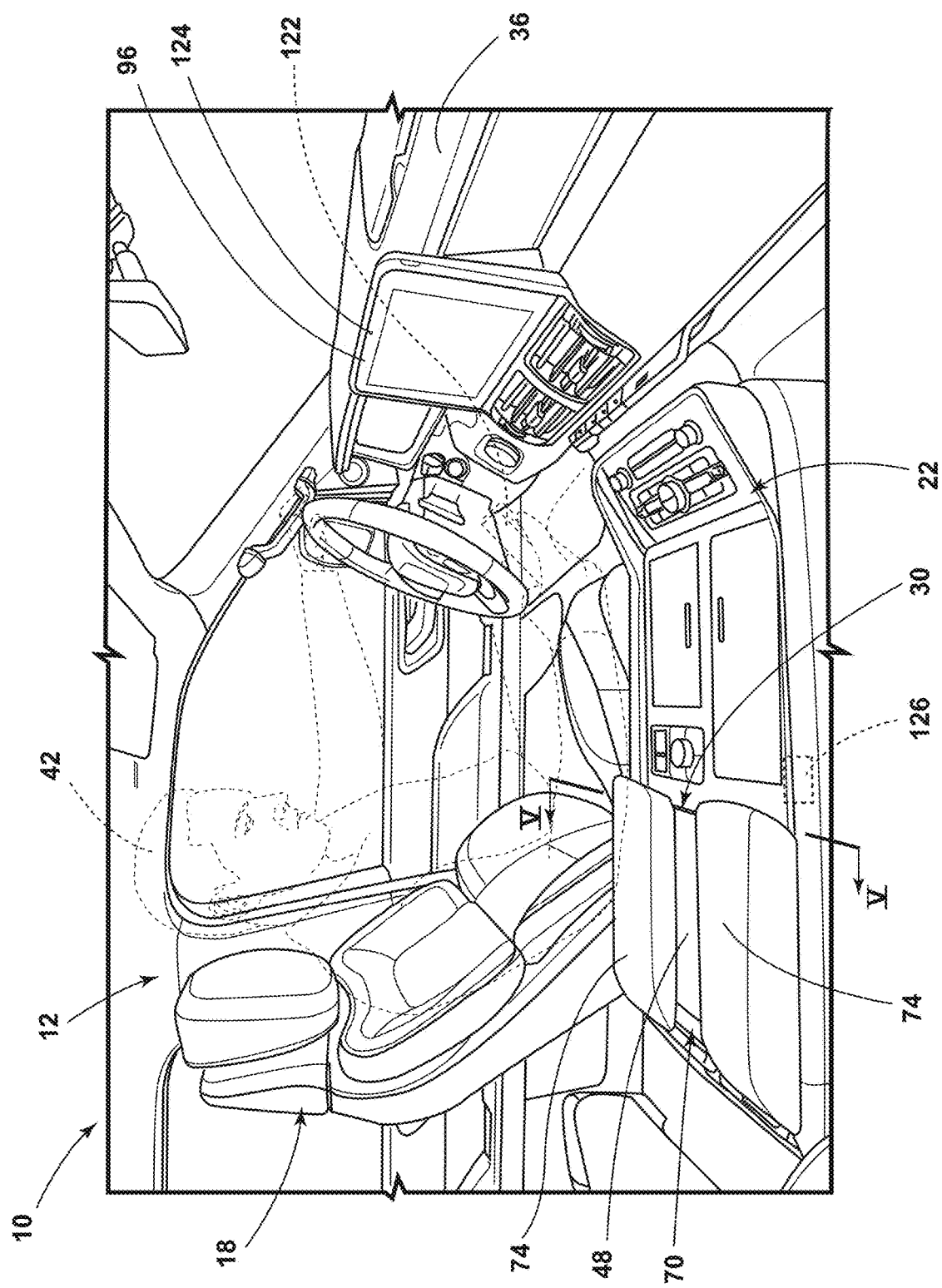
FIG. 3 is a perspective view looking portside within the interior of the vehicle, illustrating a passenger sitting in one of the seating assemblies adjacent to the treatment apparatus, and the treatment apparatus including a door in a closed position that supports several armrests.
Figure 4:
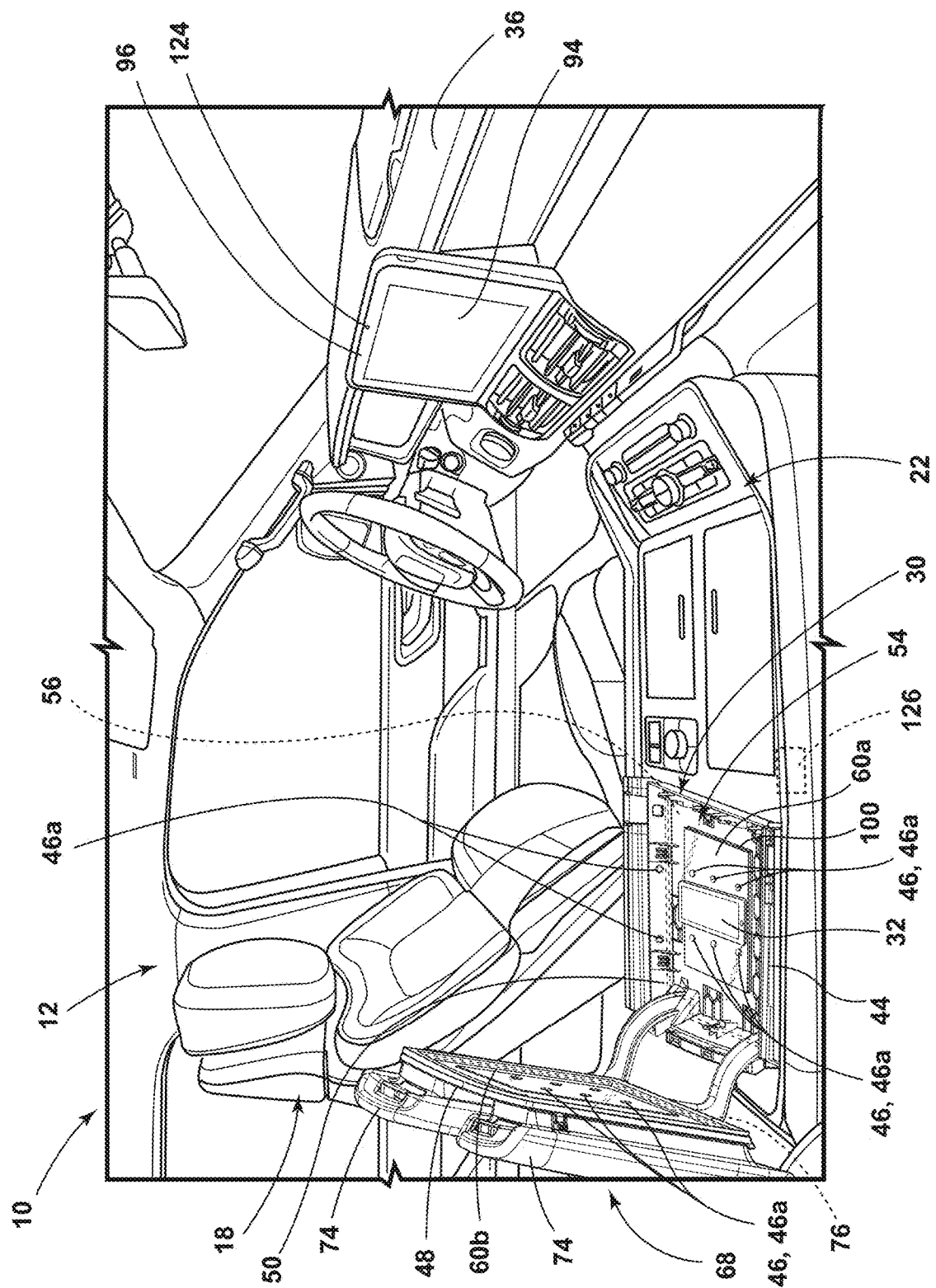
FIG. 4 is the same perspective view as FIG. 3 but illustrating the door of the treatment apparatus in an open position allowing access from the interior of the vehicle into a treatment chamber, and a housing of the treatment apparatus that supports a platform on which an object to be treated with ultraviolet light is placed.
Figure 5:
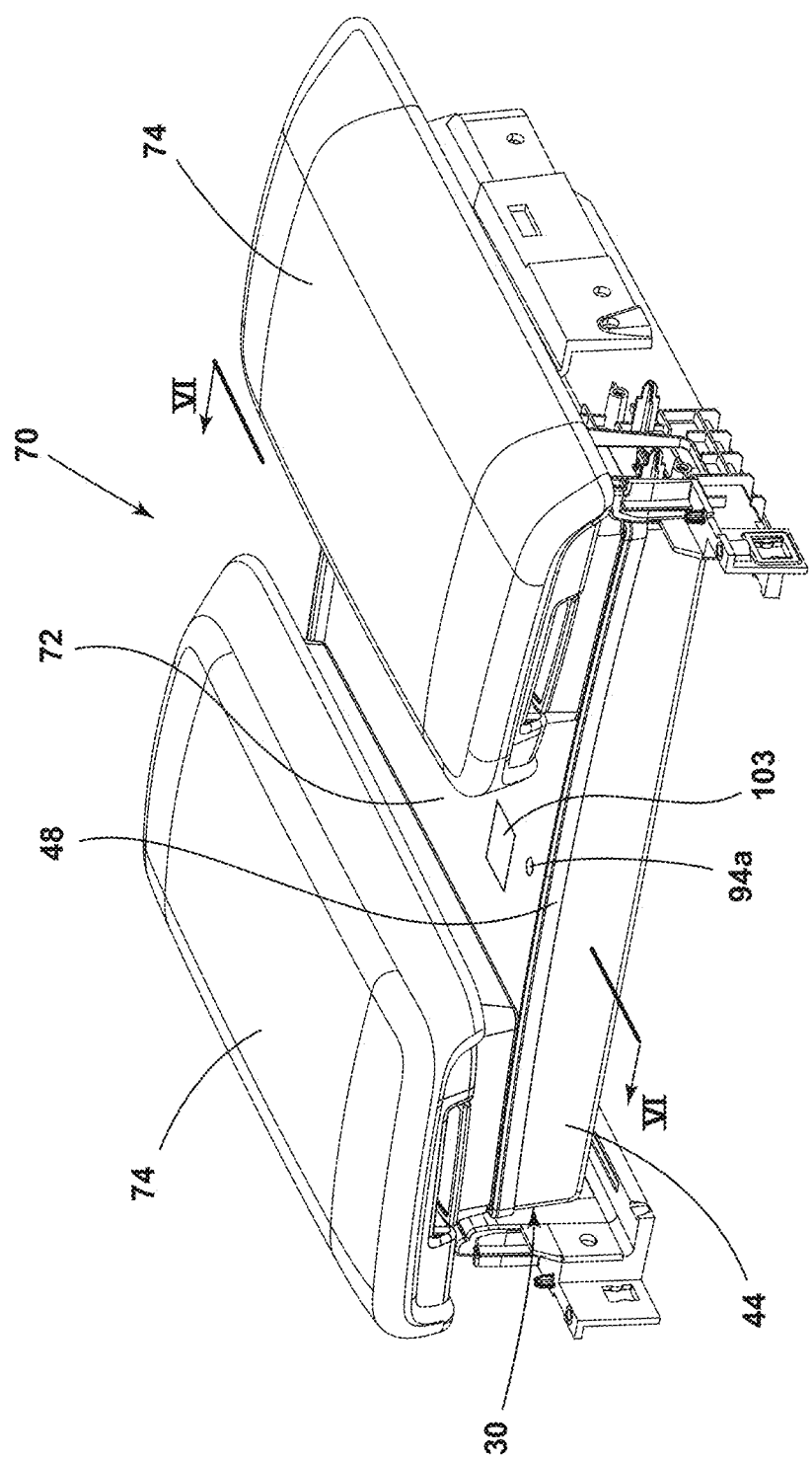
FIG. 5 is a perspective view of the treatment apparatus, illustrating the door in the closed position that denies access from the interior of the vehicle to the treatment chamber, as well as an LED display disposed on an outside portion of the door between the armrests to indicate (by emitting light within the visual spectrum) that the ultraviolet light is being emitted within the treatment chamber.
Figure 6:
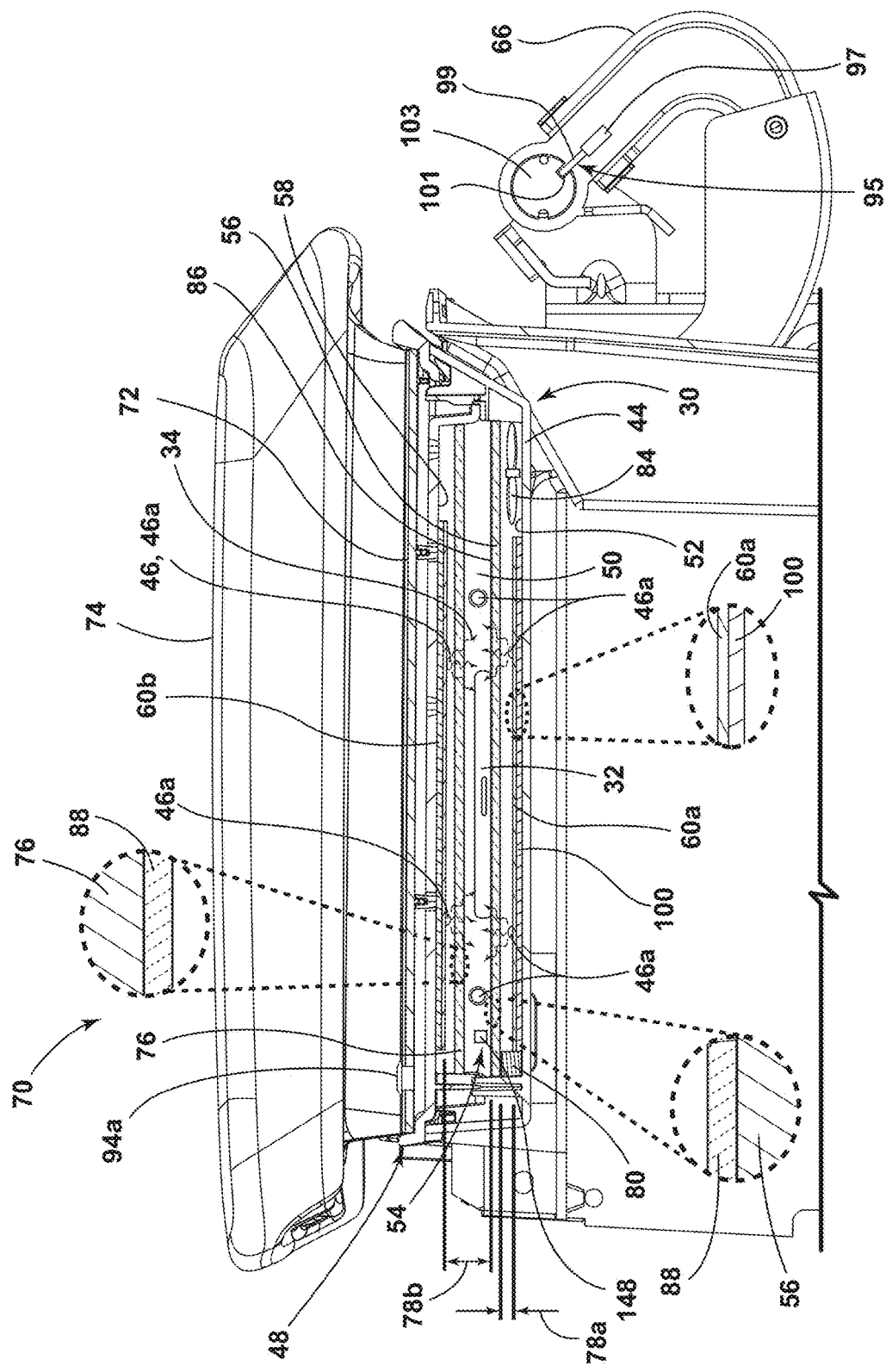
FIG. 6 is an elevational cross sectional view of the treatment apparatus taken through line VI-VI of FIG. 5, illustrating the housing of the treatment apparatus including a floor, a printed control board ("PCB") with ultraviolet light emitting diodes ("UV LEDs") and a metal heatsink above the floor, and a platform transparent to ultraviolet light above the UV LEDs to hold the object to be treated with ultraviolet light (to reduce the amount of pathogens thereupon)
Figure 7:
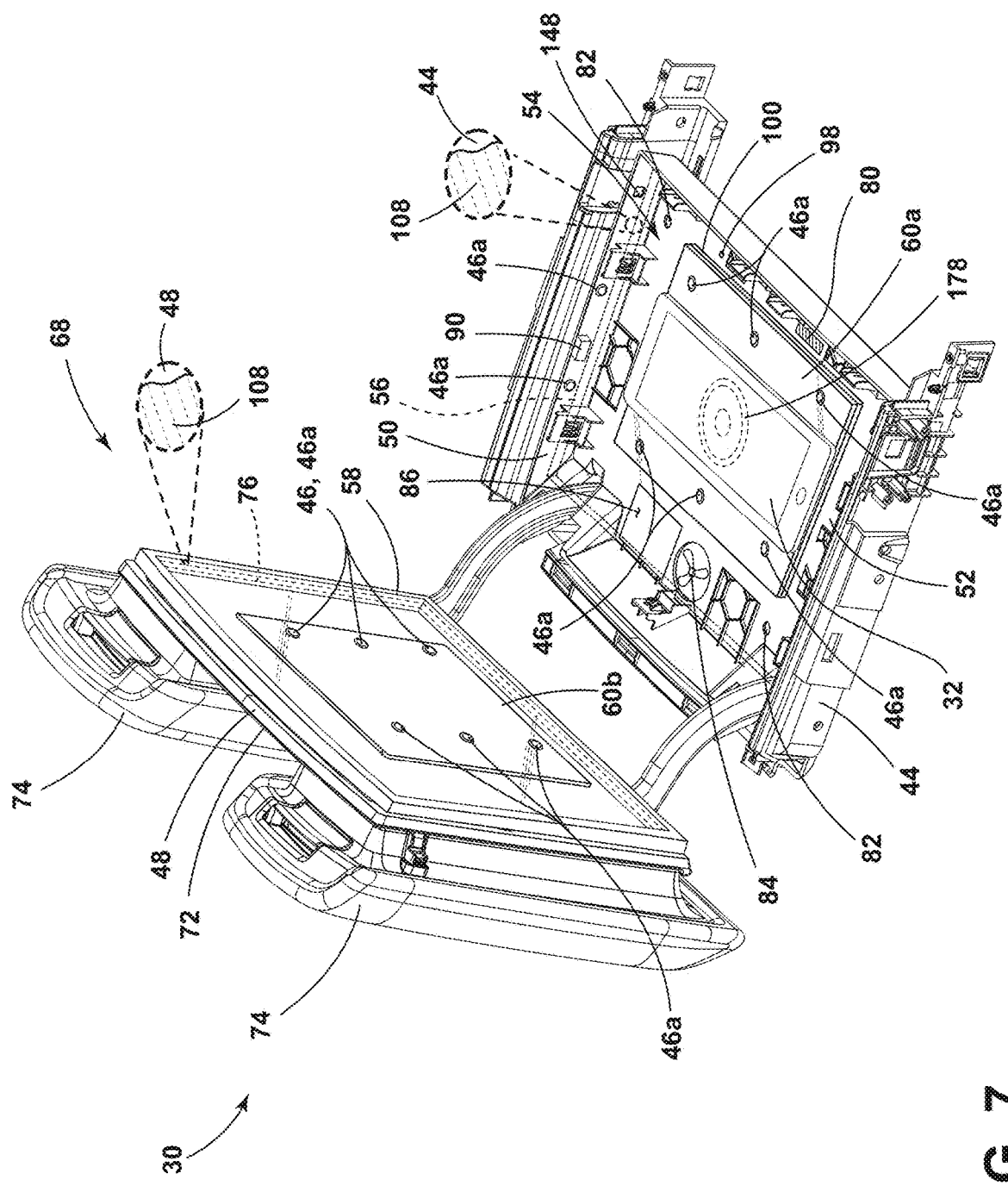
FIG. 7 is a perspective view of the treatment apparatus with the door in the open position, illustrating a wall of the housing additionally supporting UV LEDs, and the door additionally supporting UV LEDs with a barrier transparent to ultraviolet light protecting the UV LEDs from physical contact.

Referring now to FIGS. 1-7, a vehicle 10 includes an interior 12. The vehicle 10 further includes a first row of seating 14 and, in the illustrated embodiment, a second row of seating 16. The vehicle 10 can further include additional rows of seating (not illustrated). The first row of seating 14 includes seating assemblies 18 and 20, and a center console 22 disposed between the seating assemblies 18 and 20. The second row of seating 16 likewise includes seating assemblies 24 and 26, and a second center console 28 disposed between the seating assemblies 24 and 26. The vehicle 10 further includes a treatment apparatus 30 to treat an object 32 with ultraviolet light 34, as will be further discussed herein. In the illustrated embodiment, the treatment apparatus 30 is disposed at the center console 22. However, in other embodiments, the treatment apparatus 30 is disposed at the second center console 28, at a dashboard 36 (such as within a glove compartment 38), or at an overhead console 40. The vehicle 10 can be a car, truck, sports utility vehicle, off-road vehicle, a high-performance vehicle, or any other transportation apparatus. The vehicle 10 can be used for ride-sharing, ride-hailing, vehicle-sharing, public, or private purposes. The vehicle 10 can be autonomous or passenger 42 operated. The vehicle 10 can be propelled by an electric motor, an internal combustion engine, or both.

The treatment apparatus 30 includes a housing 44, a source of ultraviolet light 46, and a door 48 connected to the housing 44. The housing 44 includes at least one wall 50 and a floor 52. The at least one wall 50 and the floor 52 together form a treatment chamber 54. In embodiments, as illustrated, the wall 50 extends upward from the floor 52 and forms a contiguous perimeter around the floor 52. In embodiments, as illustrated, the treatment apparatus 30 further includes a platform 56 disposed above the floor 52 to hold the object 32 above the source of ultraviolet light 46. The housing 44 can be formed of polypropylene, although other plastics and other materials can be utilized. The platform 56 is transparent to ultraviolet light 34 (e.g., at least 80 percent transmittance). For example, the floor 52 can have a glass composition. The object 32 is disposed within the treatment chamber 54 to receive the ultraviolet light 46.

The source of ultraviolet light 46 is configured to emit ultraviolet light 34 into the treatment chamber 54. Ultraviolet light 34 herein means electromagnetic radiation having wavelengths within the range of 10 nm to 400 nm, such as 100 nm to 400 nm, 200 nm to 350 nm, 240 nm to 280 nm, and 260 nm to 270 nm. The source of ultraviolet light 46 can emit, in addition to ultraviolet light 34, electromagnetic radiation having wavelengths outside of those ranges such as within the visible spectrum (referred to as "visible light").

In embodiments, as illustrated, the source of ultraviolet light 46 includes a light emitting diode 46a (hereinafter referred to as "UV LED") that, when activated, emits ultraviolet light 34. In embodiments, as illustrated, the source of ultraviolet light 46 includes a plurality of UV LEDs 46a. The UV LEDs 46a are coupled to the housing 44, including between the platform 56 and the floor 52. The UV LEDs 46a are positioned to emit the ultraviolet light 34 into the treatment chamber 54 and through the platform 56 if included beneath the platform 56. Additional UV LEDs 46a are positioned on the wall 50 and at an inside portion 58 of the door 48, each positioned to emit ultraviolet light 34 into the treatment chamber 54. In embodiments, there are 10 UV LEDs 46a or less, such as between 6 and 10 UV LEDs 46a. In other embodiments, as in the illustrated embodiment, there are more than 10 UV LEDs 46a. The UV LEDs 46a can include an aluminum nitride substrate. In embodiments, the UV LEDs 46a have a characteristic viewing angle of 105 degrees, a forward voltage of 8.45 V at 350 mA, consume 1 to 4 W of electrical power, and emit ultraviolet light 34 with irradiance flux of 10 to 100 mW/cm$^2$. The UV LEDs 46a can be organic LEDs. In other embodiments, the source of ultraviolet light 46 is one or more vapor discharge lamps such as mercury vapor lamps.

In embodiments, the UV LEDs 46a coupled to the housing 44 are connected to a printed circuit board 60a that is fastened to the housing 44. The printed circuit board 60a can be attached to the housing 44 above the floor 52 and beneath the platform 56. The UV LEDs 46a disposed at the door 48 can likewise be attached to a printed circuit board 60b that is attached to the inside portion 58 of the door 48. The printed circuit board 60a can be generally parallel to the printed circuit board 60b.

Figure 8:
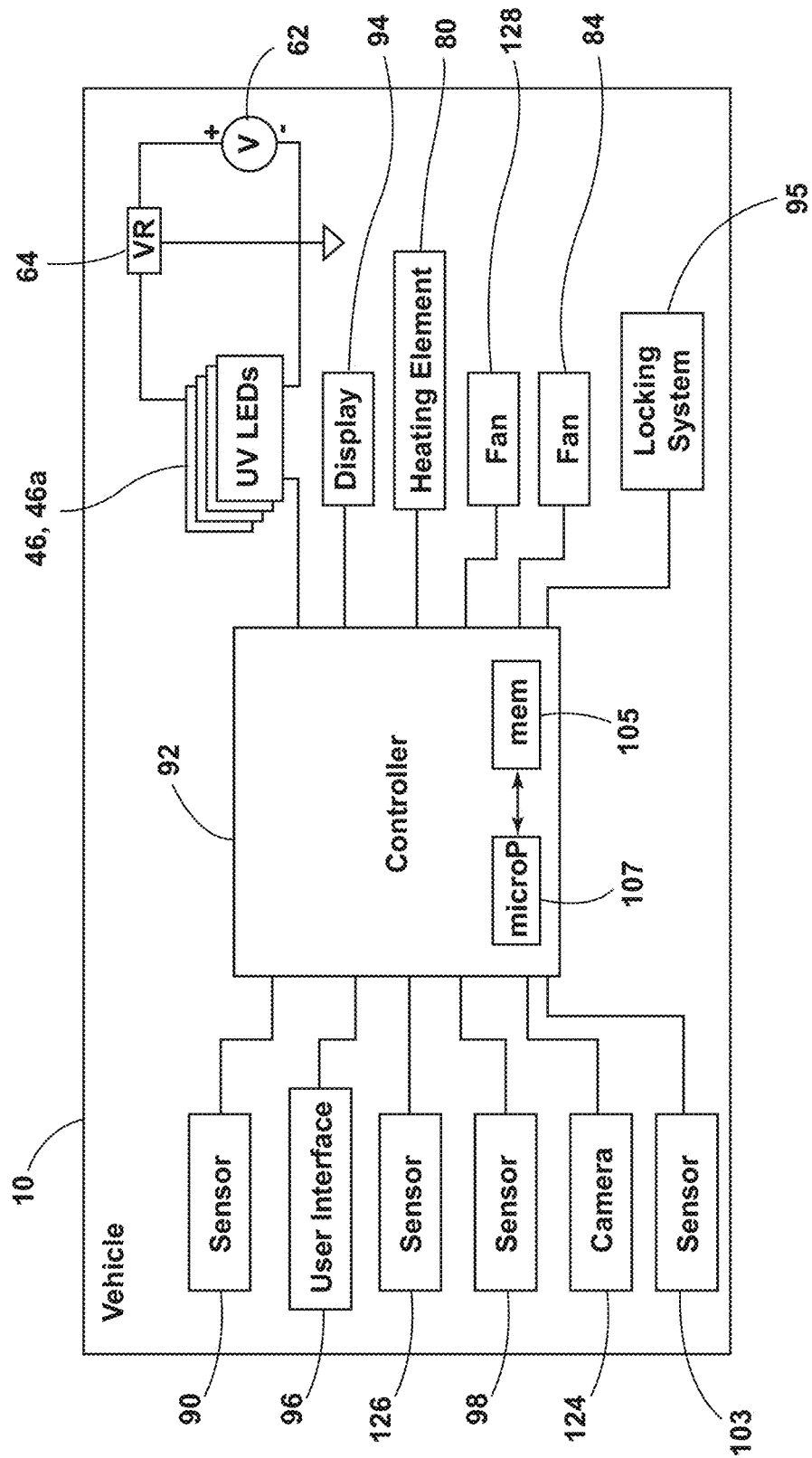
FIG. 8 is a schematic diagram of a controller of the treatment apparatus, illustrating the controller in communication with and receiving input from a variety of sensors (e.g., to determine temperature within the housing, to determine when the door is in the closed position, and to detect the presence of airborne particulate matter originating from the treatment chamber), a user interface, and a camera, the controller controlling the UV LEDs (or some other source of ultraviolet light), a display, a heating element within the housing, a fan in communication with the housing, and a fan that creates an airflow from the treatment chamber to the sensor that detects the presence of airborne particulate matter originating from the treatment chamber.

Referring now additionally to FIG. 8, in embodiments, the vehicle 10 further includes a power source 62 (e.g., a battery) that powers the UV LEDs 46a and a voltage regulator 64 disposed in electrical communication between the power source 62 and the UV LEDs 46a. The power source 62 may provide a voltage (e.g., 12 V) that is different than the operating voltage (e.g., 8.45 V) of the UV LEDs 46a, and the voltage regulator 64 can decrease the voltage from the power source 62 to the UV LEDs 46a (e.g., 12 V to 8.45 V). The voltage regulator 64 can provide up to 500 mA of current at up to 4 W of power.

The door 48 is connected to the housing 44, such as via a hinge 66. The door 48 has an open position 68 that provides access into the treatment chamber 54. In addition, the door 48 has a closed position 70 that denies access to the treatment chamber 54. When the door 48 is in the closed position 70, the inside portion 58 forms part of the treatment chamber 54. As the door 48 transitions from the closed position 70 to the open position 68, the inside portion 58 of the door 48 moves away from the floor 52 of the housing 44. The door 48 further includes an outside portion 72 that is open to the interior 12 of the vehicle 10. The outside portion 72 can support interior comfort items such as armrests 74. The door 48 can further include a barrier 76 to prevent access from the interior 12 to the source of ultraviolet light 46 (such as UV LEDs 46a) disposed at the door 48. The barrier 76 is transparent to the ultraviolet light 34 to allow transmission of the ultraviolet light 34 from the source of ultraviolet light 46 at the door 48 to the object 32 in the treatment chamber 54. The barrier 76 can be made of a glass substrate.

The door 48, together with the housing 44, prevents emitted ultraviolet light 34 from irritating beyond the treatment chamber 54. The inside portion 58 of the door 48 is contiguous, without holes that would allow emitted ultraviolet light 34 to transmit to the interior 12 of the vehicle 10. In the closed position 70, the door 48 forms a seal with a housing 44 that is sufficiently tight to prevent emitted ultraviolet light 34 to transmit to the interior 12 of the vehicle 10. The door 48, like the housing 44, is formed of a material such as plastic that does not transmit ultraviolet light 34.

As will be further discussed below, in use, the passenger 42 of the vehicle 10 places the object 32 to be treated with ultraviolet light 34 onto the platform 56 of the housing 44 within the treatment chamber 54 and places the door 48 into the closed position 70. The object 32 can be any item that fits within the treatment chamber 54 and allows the door 48 to move to the closed position 70. The object 32 can be a smartphone, a tablet computer, some other mobile electronic device, a set of headphones, a key, a watch, a toothbrush, eye glasses, a baby item (such as a pacifier), an eating utensil (such as a fork, spoon, knife), a drinking cup, or a piece of food (such as a raw fruit or vegetable). The preceding list is not exhaustive. More than one object 32 can be placed into the treatment chamber 54 at one time.

In embodiments, the treatment apparatus 30 further includes a heating element 80 in thermal communication with the treatment chamber 54. In the illustrated embodiment, the heating element 80 is disposed on the floor 52 of the housing 44 beneath the platform 56. Circulation apertures 82 can be disposed through the platform 56 to allow air that the heating element 80 heats to flow throughout the treatment chamber 54. A fan 84 can assist in this circulation of the air. The heating element 80 can be utilized to ensure that the treatment chamber 54 and the source of ultraviolet light 46 are above a predetermined minimum temperature (e.g., 20° C.) to ensure that a cooler temperature is not disadvantageously limiting the irradiance flux of the source of ultraviolet light 46, which varies as function of temperature. The heating element 80 can be a Peltier thermoelectric device.

In embodiments, a distance 78a separates the source of ultraviolet light 46 (such as UV LEDs 46a) coupled to the housing 44 from a top surface 86 of the platform 56 upon which the object 32 (if present) rests. Similarly, a distance 78b separates the source of ultraviolet light 46 (such as UV LEDs 46a) coupled to the door 48 from the top surface 86 of the platform 56. Because the irradiance flux upon the object 32 decreases as a function of distance 78 from the source of ultraviolet light 46, the distances 78a, 78b are advantageously minimized. In embodiments, one or both of the distances 78a, 78b is 10 cm or less, such as 5 cm or less, or about 2 cm.

In embodiments, a bandpass filter 88 is disposed between the source of ultraviolet light 46 and the treatment chamber 54. The bandpass filter 88 filters the ultraviolet light 34 that the source of ultraviolet light 46 emits before the ultraviolet light 34 enters the treatment chamber 54. In the illustrated embodiment, the bandpass filter 88 is a film or coating disposed over platform 56 and the barrier 76. In embodiments, the bandpass filter 88 transmits a greater percentage of ultraviolet light 34 having a wavelength of 240 nm to 280 nm than ultraviolet light 34 having a wavelength of 290 nm to 400 nm. In embodiments, the bandpass filter 88 transmits less than 10 percent of ultraviolet light 34 having a wavelength of 290 nm to 400 nm but transmits greater than 10 percent of ultraviolet light 34 having a wavelength of 240 nm to 280 nm. The bandpass filter 88 helps prevent emitted ultraviolet light 34 of wavelengths from reaching the treatment chamber 54 that would not kill pathogens on the object 32 but might deteriorate plastic components of the object 32 or the housing 44 or the door 48.

In embodiments, the source of ultraviolet light 46 does not emit ultraviolet light 34 when the door 48 is in the open position 68. This measure prevents the source of ultraviolet light 46 from emitting ultraviolet light 34 into the interior 12 of the vehicle 10, which might deteriorate plastic components of the vehicle 10 open to the interior 12. Rather, the source of ultraviolet light 46 emits ultraviolet light 34 only when the door 48 is in the closed position 70.

In embodiments, the treatment apparatus 30 further comprises a sensor 90 that produces output that varies as a function of the door 48 being in the open position 68 or in the closed position 70. In other words, the output of the sensor 90 when the door 48 is in the open position 68 is distinguishable from the output of the sensor 90 when the door 48 is in the closed position 70. The sensor 90 can be disposed at housing 44, such as at the wall 50. The sensor 90 can be a capacitive sensor, an optical sensor (e.g., an infrared sensor), an electrical on/off switch, among other options.

Referring again to FIG. 8, the treatment apparatus 30 (or the vehicle 10 generally) further includes a controller 92. The controller 92 is in communication with the source of ultraviolet light 46. The controller 92 controls activation and deactivation of the source of ultraviolet light 46—that is, whether the source of ultraviolet light 46 emits ultraviolet light 34. This measure prevents the source of ultraviolet light 46 from emitting ultraviolet light 34 into the interior 12 of the vehicle 10, which might deteriorate plastic components of the vehicle 10 open to the interior 12. The controller 92 can be a microcontroller unit ("MCU"). The controller 92 includes memory 105 to store data and programs, and a microprocessor 107 that executes those programs based using that data. In embodiments, the controller 92 is an MCU that is separated from the source of ultraviolet light 46—that is, the MCU is mounted on a printed circuit board that is different than the printed circuit boards 60a, 60b upon which the sources of ultraviolet light 46 are pointed. In embodiments, the housing 44 houses the controller 92. In other embodiments, the controller 92 is disposed beneath the seating assembly 18 or beneath the dashboard 36.

The controller 92 is in communication with the sensor 90. If the controller 92 had activated the source of ultraviolet light 46, the controller 92 deactivates the source of ultraviolet light 46 when the sensor 90 produces an output to the controller 92 from which the controller 92 determines that the door 48 is in the open position 68. In other words, the controller 92 utilizes the sensor 90 as a shut-off mechanism to disable the source of ultraviolet light 46 except when the door 48 is determined, based on output from the sensor 90, to be in the closed position 70.

Figure 9:
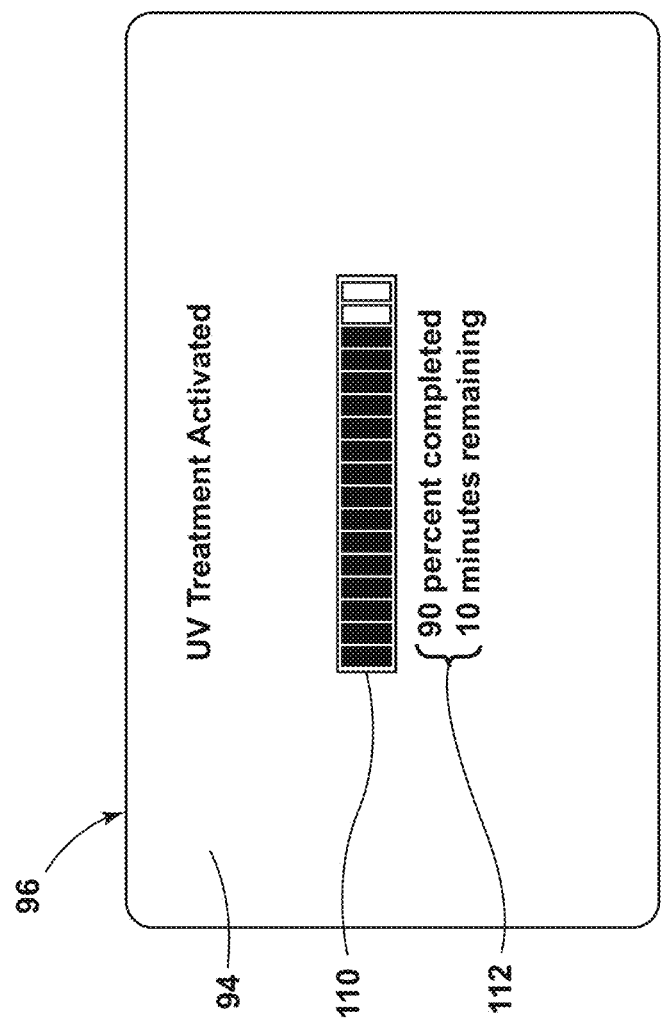
FIG. 9 is a view of the user interface that includes the display, illustrating a graphic bar and text displaying the progress and remaining duration of the treatment of the object with ultraviolet light.

Referring additionally to FIG. 9, in embodiments, the treatment apparatus 30 (or the vehicle 10 generally) further includes a display 94. The controller 92 is in communication with the display 94. The display 94 provides a visual indication that the source of ultraviolet light 46 is emitting ultraviolet light 34. The controller 92 causes the display 94 to provide the visual indication that the source of ultraviolet light 46 is emitting ultraviolet light 34 when the controller 92 is causing the source of ultraviolet light 46 to emit ultraviolet light 34. For example, the display 94 can be a multi-color LED 94a that emits light of one color (e.g., violet or red) when the source of ultraviolet light 46 is emitting ultraviolet light 34, and a light of another color (e.g., blue or green) when the source of ultraviolet light 46 is not emitting ultraviolet light 34 (such as after the conclusion of the treatment of the object 32). As another example, the display 94 can display text such as "UV Treatment Activated," "UV Treatment Deactivated," or "UV Treatment Complete." The display 94 can be located on the door 48 and be visible from the interior 12 of the vehicle 10, or the display 94 can be part of a user interface 96, which can be located at the dashboard 36. The passenger 42 is less likely to open the door 48 while the source of ultraviolet light 46 is emitting ultraviolet light 34 when the display 94 informs the passenger 42 that the source of ultraviolet light 46 is emitting ultraviolet light 34. This measure prevents the source of ultraviolet light 46 from emitting ultraviolet light 34 into the interior 12 of the vehicle 10, which might deteriorate plastic components of the vehicle 10 open to the interior 12.

In embodiments, the treatment apparatus 30 further includes a locking system 95. The locking system 95 is in communication with the controller 92. The locking system 95 prevents the door 48 from transitioning from the closed position 70 (such as to the open position 68) while the source of ultraviolet light 46 is emitting ultraviolet light 34 into the treatment chamber 54. The locking system 95 can include an actuator 97 with a piston 99 attached to the hinge 66, and a receiver 101 for the piston 99 attached not to the hinge 66, such as an axle 103 about which the hinge 66 rotates. When the controller 92 is causing the source of ultraviolet light 34 to emit ultraviolet light 34, the controller 92 causes the actuator 97 to extend the piston 99 into the receiver 101, which thus prevents the hinge 66 from rotating about the axle 103 and thus the door 48 from moving away from the closed position 70. When the controller 92 is not causing the source of ultraviolet light 34 to emit ultraviolet light 34, the controller 92 causes the actuator 92 to retract the piston 99 from the receiver 101, which allows the hinge 66 to rotate about the axle 103 and thus allow the door 48 to move away from the closed position 70 to the open position 68. This measure prevents the source of ultraviolet light 46 from emitting ultraviolet light 34 into the interior 12 of the vehicle 10, which might deteriorate plastic components of the vehicle 10 open to the interior 12.

In embodiments, the treatment apparatus 30 further includes a sensor 103 that produces output that varies as a function of whether the passenger 42 is touching the sensor 103. The sensor 103 is in communication with the controller 92. The sensor 103 can be a capacitive sensor or some other touch sensitive sensor, such as a button. The sensor 103 can be disposed at the door 48 such as an outside portion 72 thereof. By touching the sensor 103, the passenger 42 can indicate that the passenger 42 would like to transition the door 48 to the open position 68, such as to retrieve the object 32 from the treatment chamber 54 before the treatment with ultraviolet light 34 has ended. The sensor 103 produces the output indicative of the passenger 42 touching the sensor 103, the controller 92 as a consequence of receiving the output causes the source of ultraviolet light 46 to cease emitting ultraviolet light 34 and, if implemented, causes the locking system 95 to unlock and allow the door 48 to move away from the closed position 70 to the open position 68. The controller 92 can require the sensor 103 to produce such output for a predetermined period of time (e.g., 3 seconds) before causing the source of ultraviolet light 46 to cease emitting ultraviolet light 34, to prevent unintentional deactivation of the source of ultraviolet light 46. This measure prevents the source of ultraviolet light 46 from emitting ultraviolet light 34 into the interior 12 of the vehicle 10, which might deteriorate plastic components of the vehicle 10 open to the interior 12, but also allows the passenger 42 to retrieve the object 32.

In embodiments, the treatment apparatus 30 further includes a sensor 98 positioned to produce output that varies as a function of the temperature of the source of ultraviolet light 46 or the printed circuit board 60a upon which the source of ultraviolet light 46 is mounted. For example, the sensor 98 can be placed between the floor 52 and the platform 56. The sensor 98 can be a thermistor. The sensor 98 is in communication with the controller 92. After the controller 92 has activated the source of ultraviolet light 46, the controller 92 deactivates the source of ultraviolet light 46 as a function of the output of the sensor 98. For example, after the controller 92 has activated the source of ultraviolet light 46, the controller 92 deactivates the source of ultraviolet light 46 when the controller 92 determines, based on the output of the sensor 98, that the temperature of the source of ultraviolet light 46 or the printed circuit board 60a exceeds a predetermined temperature (such as 60° C.).

In embodiments where the treatment apparatus 30 includes the heating element 80, the controller 92 can be in communication with the heating element 80, and activate the heating element 80 when the sensor 98 generates output from which the controller 92 determines that the source of ultraviolet light 46 or the printed circuit board 60a is below a predetermined temperature (e.g., 20° C.), and deactivates the heating element 80 when the sensor 98 generates output from which the controller 92 determines that the source of ultraviolet light 46 or the printed circuit board 60a is above the predetermined temperature (e.g., 20° C.).

In embodiments, the fan 84 mentioned above is in communication with the controller 92, and the controller 92 controls activation of the fan 84. In addition to being positioned to circulate air heated by the heating element 80, the fan 84 is positioned to circulate air onto the source of ultraviolet light 46 and the printed circuit board 60a. The controller 92 can activate the fan 84 whenever the controller 92 activates the source of ultraviolet light 46. Alternatively, the controller 92 can activate the fan 84 when the sensor 98 provides output from which the controller 92 determines that the temperature of the source of ultraviolet light 46 or the printed circuit board 60a is above a predetermined temperature (e.g., 35° C.). This measure helps prevent the source of ultraviolet light 46 or the printed circuit board 60a from degrading.

Figure 10:
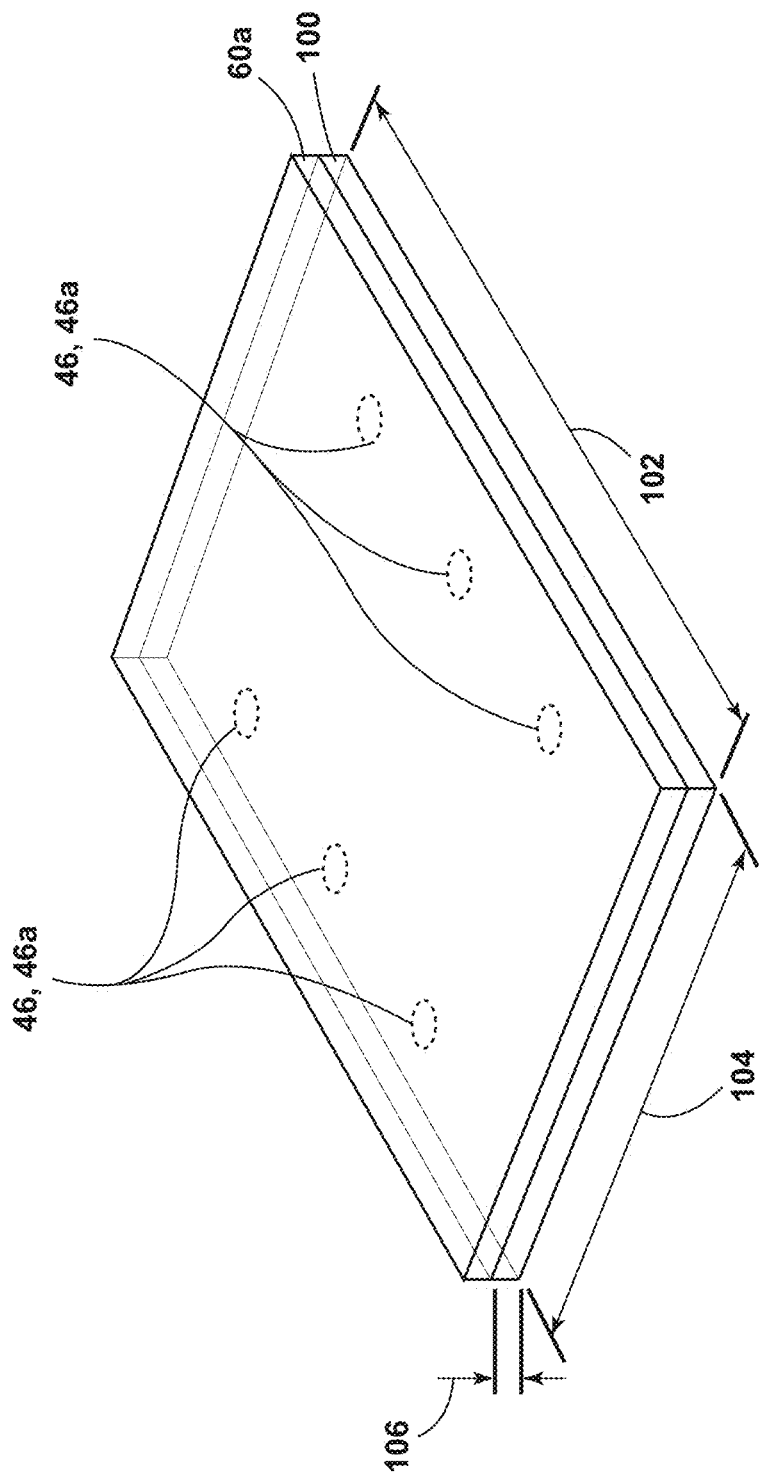
FIG. 10 is a perspective view of the PCB supporting several UV LEDs, as well as the metal heatsink attached to an underside of the PCB with thermal paste.

Referring additionally to FIG. 10, in embodiments, the treatment apparatus 30 further includes a metal heatsink 100 in thermal communication with the source of ultraviolet light 46 or the printed circuit board 60a upon which the source of ultraviolet light 46 is mounted. The metal can be aluminum or an aluminum alloy. Other metals can be utilized. The metal heatsink 100 can be sheet-like, with a length 102 and a width 104 being greater than a thickness 106 (such as at least 10 times greater than the thickness 106). The heatsink 100 can be directly attached to the printed circuit board 60a using an adhesive or otherwise. The adhesive can be a thermal paste with a thermal conductivity of 20 to 40 W/(m·K). The fan 84 likewise can circulate air over the metal heatsink 100. This measure helps prevent the source of ultraviolet light 46 or the printed circuit board 60a from degrading.

In embodiments, the treatment apparatus 30 further includes a coating 108 disposed over a portion of the housing 44, a portion of the door 48, or both that are open to the treatment chamber 54. The coating 108 reflects at least 50 percent of ultraviolet light 34 having a wavelength of 240 nm to 280 nm. The coating 108 thus reflects at least a portion of the emitted ultraviolet light 34 back into the treatment chamber 54 rather than the housing 44 or the door 48 without the coating 108 absorbing that portion of the ultraviolet light 34. The coating 108 could be a metal foil or metallic paint. This measure both increases the amount of ultraviolet light 34 irradiating onto the object 32 receiving treatment and protects otherwise exposed plastic components from possible degradation from the ultraviolet light 34.

In embodiments, the controller 92 causes the source of ultraviolet light 46 to emit ultraviolet light 34 for a predetermined period of time and, upon conclusion of the predetermined period of time, deactivates the source of ultraviolet light 46. As mentioned, the user interface 96 is in communication with the controller 92. In embodiments, the passenger 42 inputs the predetermined period of time at the user interface 96, the user interface 96 communicates the predetermined period of time to the controller 92, the controller 92 causes the source of ultraviolet light 46 to emit ultraviolet light 34 for the predetermined period of time, and, upon conclusion of the predetermined period of time, the controller 92 deactivates the source of ultraviolet light 46. This provides the passenger 42 with control over the amount of time that the object 32 is treated with ultraviolet light 34. Perhaps the passenger 42 has entered the interior 12 of the vehicle 10 as a part of a ride-sharing service and has only several minutes until the vehicle 10 arrives at the destination that the passenger 42 desires. The passenger 42 can utilize those several minutes to treat the object 32 (e.g., paper money) with ultraviolet light 34. Short periods of time can reduce the amount of pathogens on the object 32. In embodiments, the display 94 provides a graphic bar 110 or text 112 (e.g., "10 minutes remaining") or both indicating the time of the predetermined period of time remaining until the treatment has concluded.

Figure 11:
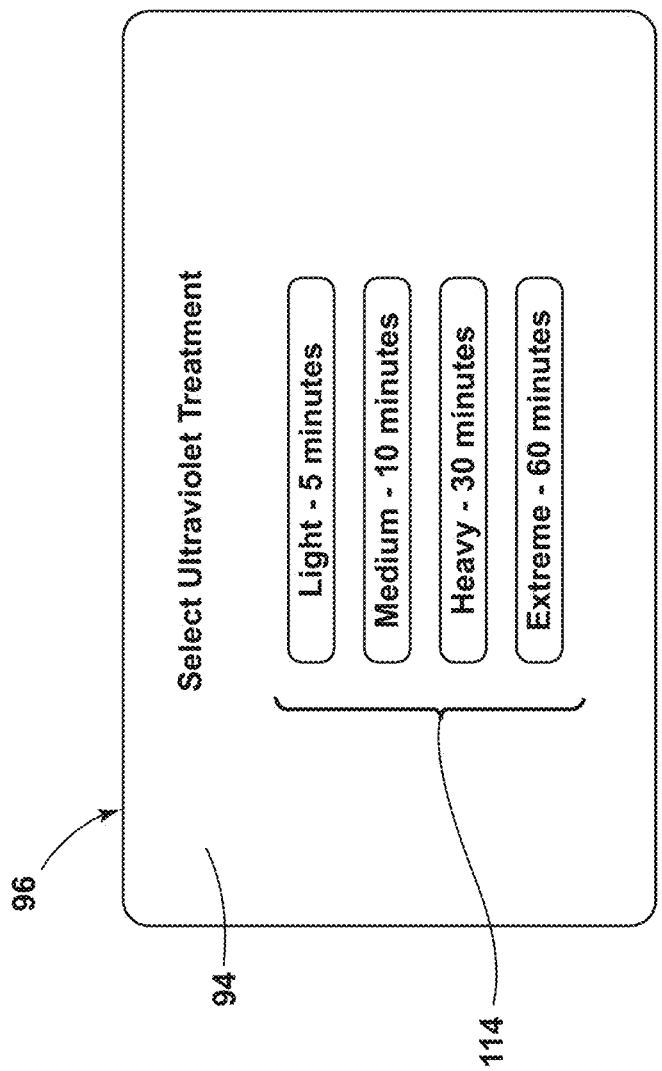
FIG. 11 is a view of the user interface that includes the display, illustrating selectable options for the passenger of the vehicle to select to set a predetermined period of time that the controller will cause the UV LEDs to emit ultraviolet light onto the object within the treatment chamber.

Referring additionally to FIG. 11, in embodiments, the user interface 96 includes the display 94 and provides the passenger 42 with selectable options 114 that identify the predetermined period of time for the passenger 42 to select. The selectable options 114 can include relative levels of treatment that are each correlated with a different predetermined period of time. For example, the display 94 can display selectable options 114 of "Light," "Medium," "Heavy," and "Extreme." The predetermined period of time for "Light" can be 1 minute to 5 minutes and can deliver up to 30,000 µJ/cm² of energy to the object 32. The predetermined period of time for "Medium" can be 5 minutes to 10 minutes and can deliver up to 60,000 µJ/cm² of energy to the object 32. The predetermined period of time for "Heavy" can be 10 minutes to 30 minutes and can deliver up to 120,000 µJ/cm² of energy to the object 32. The predetermined period of time for "Extreme" can be 30 minutes to 60 minutes and can deliver up to 360,000 µJ/cm² of energy to the object 32. These selectable options 114 are not exclusive and are for illustrative purposes. More or less relative levels of treatment can be provided as the selectable options 114, and the relative levels of treatment can be correlated with different predetermined periods of time to deliver different µJ/cm² of energy to the object 32 than those stated.

Figure 12:
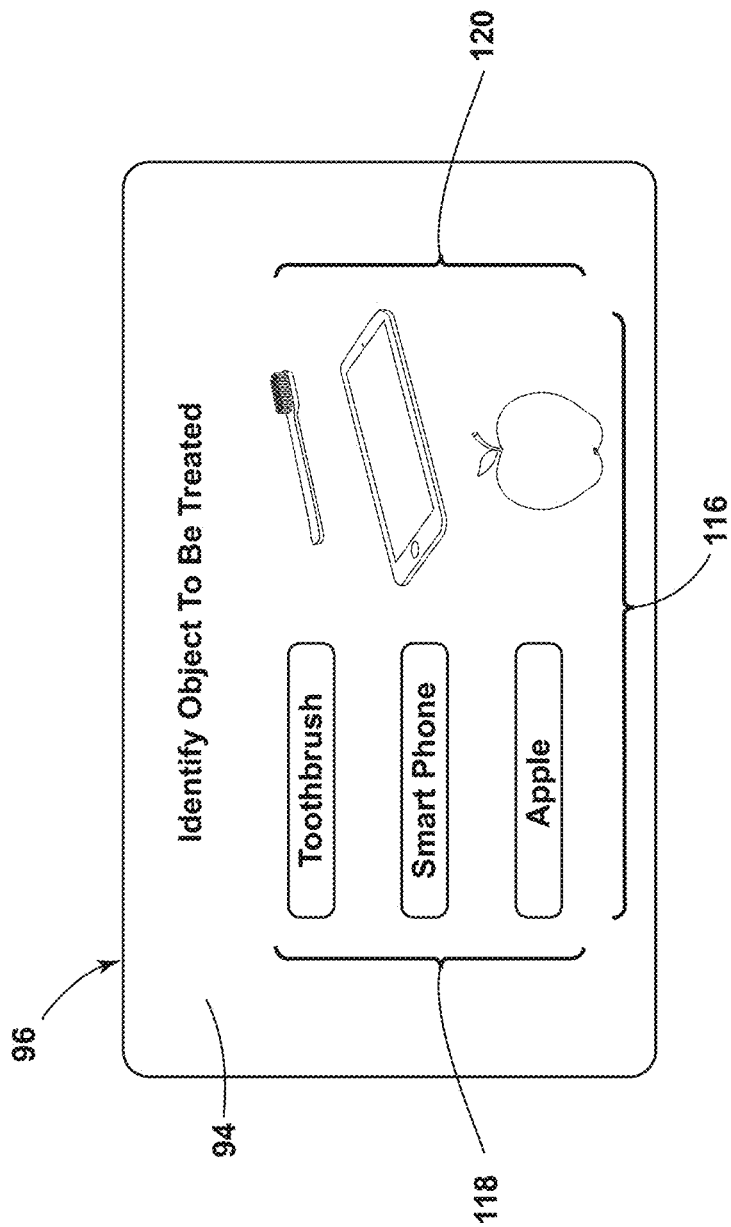
FIG. 12 is a view of the user interface that includes the display, illustrating selectable options for the passenger of the vehicle to categorize the object to be treated with ultraviolet light, with the controller determining the predetermined period of time based on the selected selectable option.

Referring additionally to FIG. 12, in embodiments, the user interface 96 includes the display 94 and provides the passenger 42 with selectable options 116 that identify the object 32 to be treated in the treatment chamber 54 with ultraviolet light 34. The selectable options 116 could be text 118 (e.g., "toothbrush," "smart phone," "apple," etc.). The selectable options 116 could be illustrations 120 of various types of objects 32 (e.g., a picture of a toothbrush, a picture of a smart phone, a picture of an apple, etc.). After the passenger 42 chooses the selectable option 116 (e.g., touches the display at the word "toothbrush"), the user interface 96 communicates this selection as output to the controller 92. The controller 92 determines the predetermined period of time as a function of the selected, selectable option 116. The controller 92 can also determine an intensity of the UV LEDs or number of UV LEDs activated as a function of the selected selectable option 116. For example, the controller 92 can assign a predetermined period of time for one type of object 32 (e.g., 5 minutes for a smart phone), and a different period of time for another type of object 32 (e.g., 10 minutes for a toothbrush). An object 32 with major surfaces not directly opposing the source of ultraviolet light 46 (e.g., an apple) can be assigned a predetermined period of time that is higher than an object 32 without such major surfaces (e.g. a smart phone). After determining the predetermined period of time from the selected, selectable option 116 of the passenger 42, the controller 92 causes the source of ultraviolet light 46 to emit ultraviolet light 34 for the predetermined period of time, and, upon conclusion of the predetermined period of time, deactivates the source of ultraviolet light 46. This measure helps ensure that the period of time that the source of ultraviolet light 46 emits ultraviolet light 34 is tailored to the object 32, therefore optimizing energy expenditure. The user interface 96 and the display 94 can be part of an infotainment system of the vehicle 10, and can communicate with the controller 92 via a controller area network ("CAN") or local interconnect network ("LIN"). In embodiments, an electronic device 122 of the passenger 42 (see FIG. 3) includes the user interface 96 and the display 94, and the controller 92 communicates via Bluetooth®, Ultra-Wide Band (UWB), Wi-Fi, or other wireless communication protocols with the electronic device 122.

In embodiments, the controller 92 determines (i) a total energy that the source of ultraviolet light 46 is to emit into the treatment chamber 54, and (ii) an intensity of ultraviolet light 34 as a function of the total energy and the predetermined period of time. More specifically, the controller 92 can be assigned to cause a total energy of 6,000 µJ to 360,000 µJ of ultraviolet light 34 to irradiate into the treatment chamber 54. For any particular predetermined period of time, the controller 92 can determine the intensity (irradiance flux) of ultraviolet light 34 from the source of ultraviolet light 46. For example, if the controller 92 is assigned to cause 100,000 µJ of total energy to be delivered to the object 32, and the predetermined period of time is 1,000 seconds, the controller 92 calculates that the intensity required is 100 µW/cm². The controller 92 causes the source of ultraviolet light 46 to emit ultraviolet light 34 at that intensity. In addition, in embodiments where the source of ultraviolet light 46 includes a number of UV LEDs, the controller 92 can cause all the UV LEDs or some portion thereof to deliver the total energy to the object 32 and adjust the intensity for each UV LEDs as a function of the number of UV LEDs chosen to deliver that total energy. One object 32 might be smaller than another object 32 and the activation of less than all of the UV LEDs could be appropriate. After the conclusion of the predetermined period of time, the controller 92 deactivates the source of ultraviolet light 46. This measure helps ensure that the period of time that the source of ultraviolet light 46 emits ultraviolet light 34 is tailored to a specific total energy expenditure, therefore optimizing energy expenditure.

In embodiments, the treatment apparatus 30 includes a camera 124. The camera 124 is in communication with the controller 92. The camera 124 is positioned to capture an image of the object 32 to be treated in the treatment chamber 54. For example, the camera 124 can be positioned at the overhead console 40 or the user interface 96. The controller 92, when receiving output from the sensor 90 that the door 48 is in the open position 68, can cause the camera 124 to capture images (image data) of the object 32 as the passenger 42 places the object 32 into the treatment chamber 54. The controller 92 can classify the object 32 from image data that the camera 124 communicates to the controller 92. The controller 92 can, based on the classification of the object 32, determine the predetermined period of time. After the passenger 42 places the door 48 in the closed position 70, the controller 92 causes the source of ultraviolet light 46 to emit ultraviolet light 34 for the predetermined period of time. Thereafter, the controller 92 deactivates the source of ultraviolet light 46. This measure helps ensure that the period of time that the source of ultraviolet light 46 emits ultraviolet light 34 is tailored to the object 32, therefore optimizing energy expenditure.

In embodiments, the camera 124 includes a Near IR (Infrared) camera positioned to capture image of the object 32 within the treatment chamber 54. This allows image recognition of the object 32 when the door 48 is in the closed position 70. An object 32 can change position within the treatment chamber 54 while the vehicle 10 is operating. The controller 92 can alter one or more of: (i) the predetermined period of time that the source of ultraviolet light 46 emits ultraviolet light 34, (ii) which particular UV LEDs of the source of ultraviolet light 46 are activated to emit ultraviolet light 34, and (iii) the intensity of emission as a function of the change in position of the object 32 within the treatment chamber 54 that the Near IR camera detected. In embodiments, the controller 92 determines from the captured NEAR IR image data that the object 32 has moved to a position within the treatment chamber 54 that is unsuitable for further treatment with ultraviolet light 34, deactivates the source of ultraviolet light 46, and causes the display 94 to display that the treatment has been deactivated. The controller 92 may optionally provide instructions to the passenger 42 to reposition the object 32 within the treatment chamber 54 to resume treatment.

In embodiments, the controller 92 determines the predetermined period of time as a function of the amount of time that has lapsed since the object 32 was last treated with ultraviolet light 34. The longer the amount of time since the last treatment, the longer the predetermined period of time for the pending treatment. The controller 92 can correlate the object 32 and date of treatment with ultraviolet light 34 and store the correlation in memory 105. The controller 92 can estimate the object 32 from the image data from the camera 124. In addition, the controller 92 can identify the object 32 when the object 32 is an electronic device that has an electronic signature such as a Bluetooth® Device Address.

Figure 13:
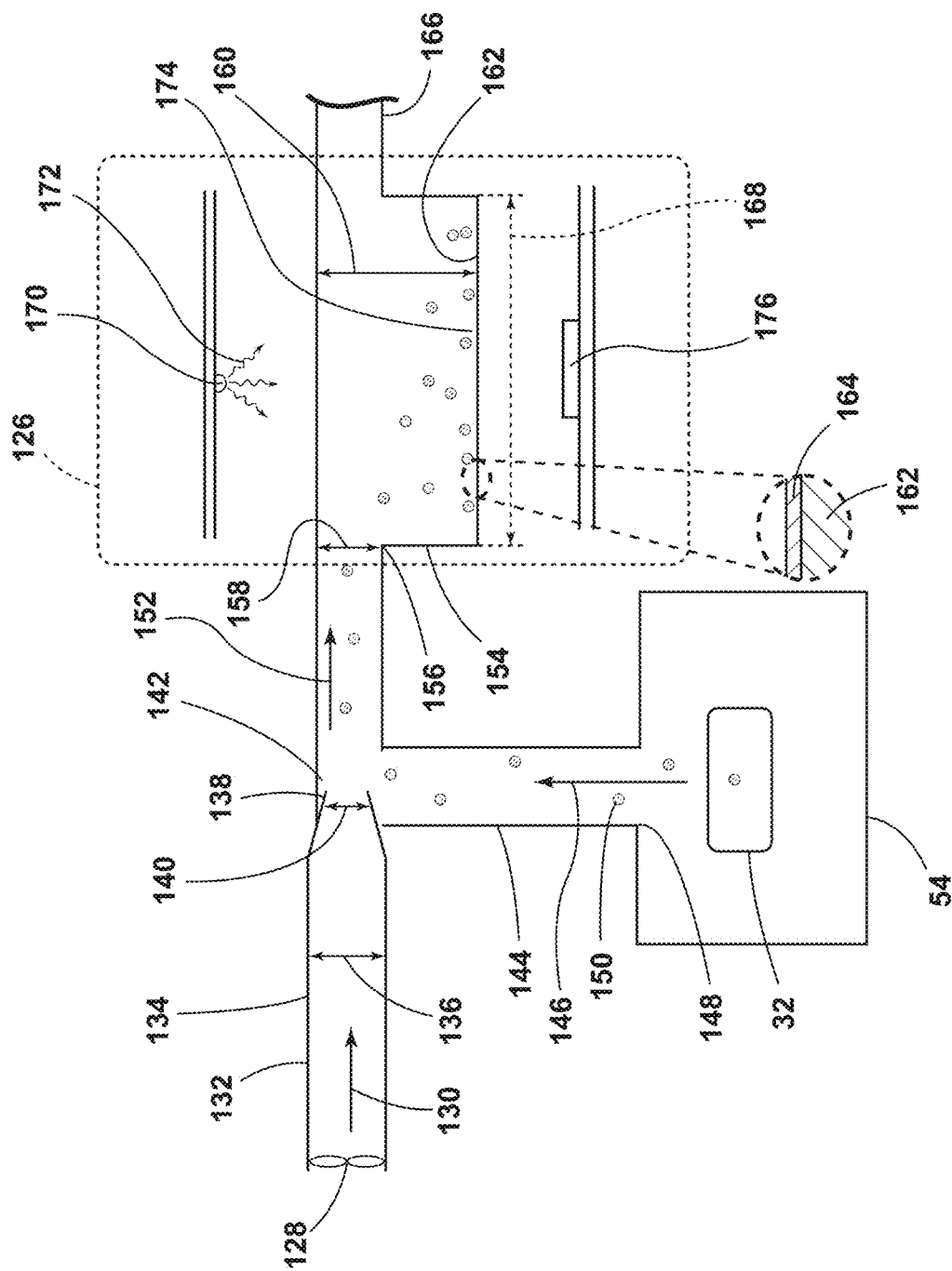
FIG. 13 is a schematic illustration of the sensor to detect the presence of airborne particulate matter originating from the treatment chamber in communication with the treatment chamber, and the sensor including a collection chamber in which airborne particulate matter is collected, a light source emitting light toward the collection chamber, and a photodetector that produces output that changes as a function of the amount of airborne particulate matter in the collection chamber.
Figure 14:
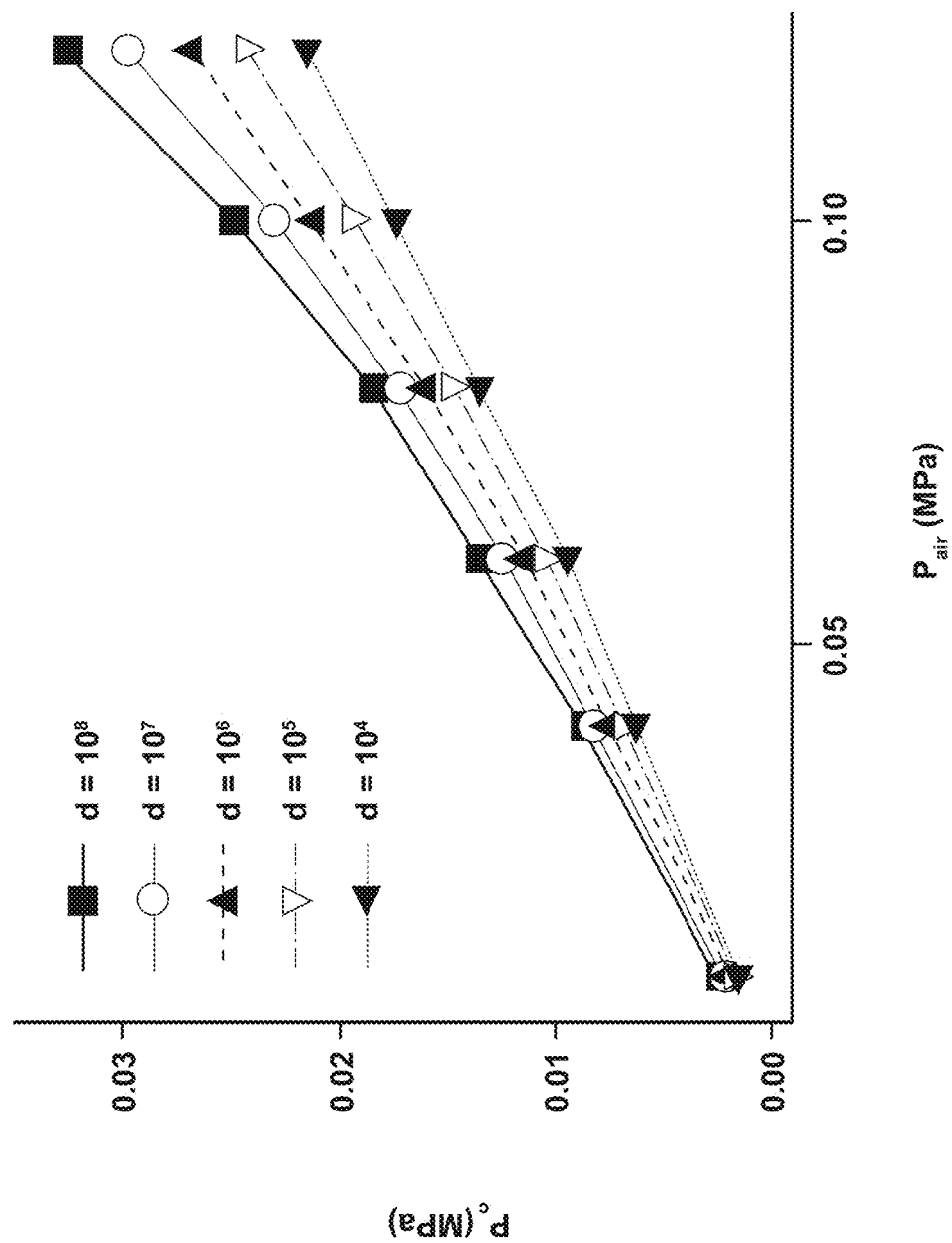
FIG. 14 is a graph of pressure of airflow pulled from the treatment chamber as a function of pressure of airflow that pulls the airflow from the treatment chamber, as well as the density of particles (representing airborne particulate matter) in the airflow from the treatment chamber.

Referring additionally to FIGS. 13 and 14, in embodiments, the treatment apparatus 30 includes a sensor 126 that collects a volume of airborne particulate matter 150. After the passenger 42 places the object 32 to be treated in the treatment chamber 54 and the door 48 is in the closed position 70, the controller 92 activates a fan 128 to cause airflow 130 through an air supply inlet 132 disposed away from the treatment chamber 54. The air supply inlet 132 includes a wider section 134 having a first inner diameter 136 and a narrower section 138 having a second inner diameter 140 downstream of the wider section 134. The second inner diameter 140 of the narrower section 138 is smaller than the first inner diameter 136 of the wider section 134. The airflow 130 exits the air supply inlet 132 at a junction 142 that is in fluidic communication with the treatment chamber 54 via a sensor line 144. Airflow 130 exiting the air supply inlet 132 at the narrower section 138 decreases the pressure within the junction 142 to below the pressure of the treatment chamber 54, which is at atmospheric pressure. The reduced pressure within the junction 142 induces airflow 146 from the treatment chamber 54 into the sensor line 144 at an inlet 148 within the treatment chamber 54. The graph reproduced at FIG. 14 shows the air pressure within the junction 142 ($P_c$ in MPa) as a function of the pressure of the airflow 130 ($P_{air}$ in MPa) for various densities of 1 μm diameter (d in number of particles per Liter of air) polystyrene beads fed in to the sensor line 144.

The induced airflow 146 flows over the object 32 and causes particulate matter (including pathogens if any) to lift from the object 32 and become airborne particulate matter 150. The airborne particular matter 150 flows with the airflow 146 from the treatment chamber 54 into the sensor line 144 through the inlet 148. Airflow 130 thus pulls airflow 146 with the airborne particulate matter 150 into the junction 142 where airflows 130, 146 combine into airflow 152 with airborne particulate matter 150.

The sensor 126 includes a collection chamber 154 downstream from the junction 142. The airflow 152 including the airborne particulate matter 150 flows from the junction 142, out an outlet 156, and into the collection chamber 154. The outlet 156 has a diameter 158. The collection chamber 154 has a height 160. The height 160 is larger than the diameter 158. The airborne particulate matter 150 has a velocity that slows as the airborne particular matter 150 flows out of the outlet 156 and into the collection chamber 154. The collection chamber 154 includes a bottom 162 and an adhesion layer 164 disposed over the bottom 162. The airborne particulate matter 150 thus settles onto the adhesion layer 164. Airflow 152 flows out of the sensor 126 at an exit 166.

Simulations reveal that the adhesion layer 164 captures nearly 100 percent of the airborne particulate matter 150 when (i) the velocity of the airborne particulate matter 150 is less than 1 meter per second at the outlet 156, and (ii) the ratio of a length 168 of the collection chamber 154 (parallel to the airflow 152) to the height 160 of the collection chamber 154 is 4 or greater. Such a ratio ensures that the velocity of the airflow 152 between the outlet 156 and the exit 166 is at least three orders of magnitude larger than the velocity of the airflow 152 near the adhesion layer 164. Shear stress thus maintains the airborne particulate matter 150 (no longer airborne) on the adhesion layer 164. In embodiments, the length 168 of the collection chamber 154 is 1.6 cm, the height 160 is 0.4 cm, and a width (not illustrated) orthogonal to the length 168 and the height 160 is 0.5 cm.

The sensor 126 is in communication with the controller 92. The sensor 126 provides output to the controller 92 that varies as a function of the volume of airborne particular matter 150 collected within the collection chamber 154. In embodiments, the sensor 126 further includes a light source 170 directing light 172 to a first side 174 of the adhesion layer 164. The light source 170 can be an LED. The light source 170 can be an indium gallium nitride LED with a peak wavelength between 400 nm and 700 nm and a peak electrical consumption of 500 nW. The light 172 illuminates the airborne particulate matter 150 (including pathogens) trapped on the adhesion layer 164.

Figure 15:
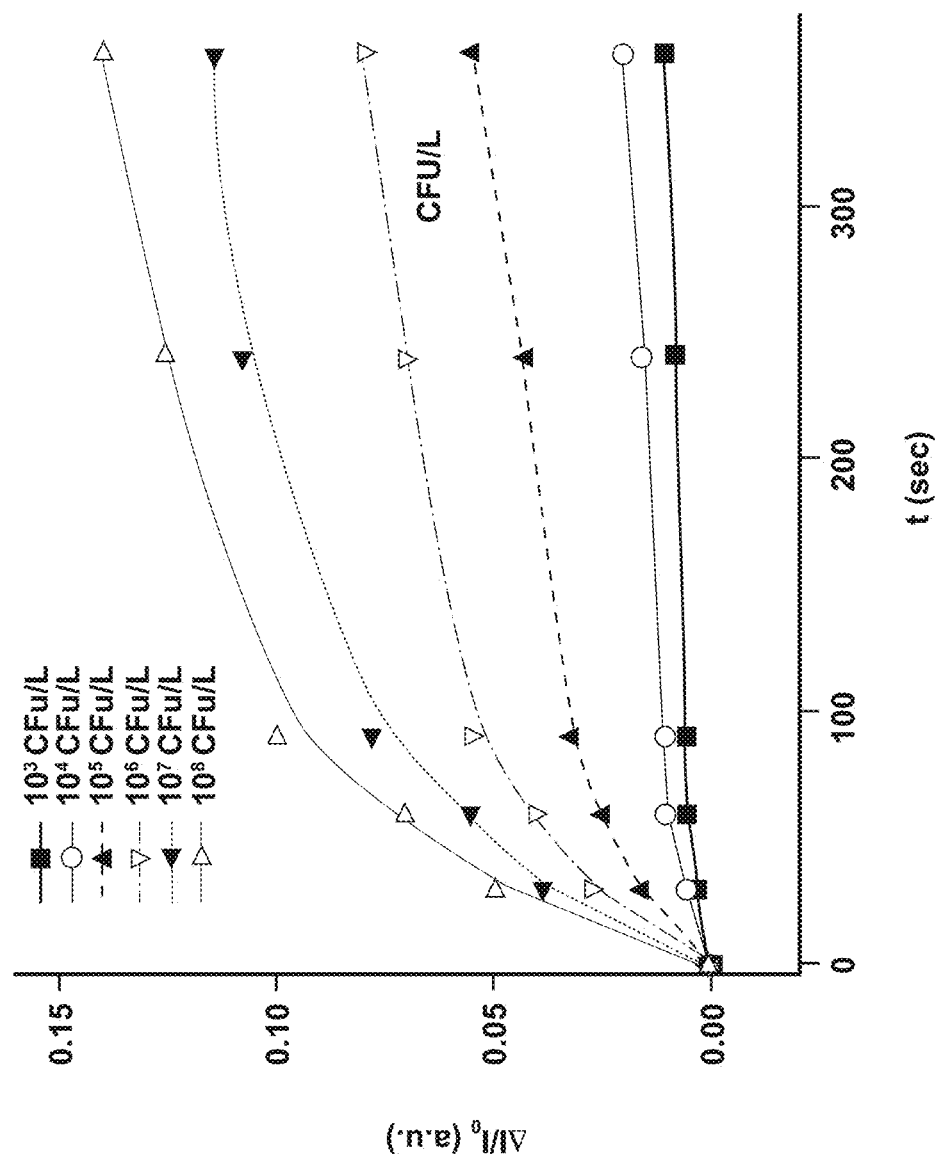
FIG. 15 is a graph of the ratio of the change in current to the baseline current of the photodetector of FIG. 13 as a function of time of airflow from the treatment chamber, as well as the density of airborne particulate matter in the treatment chamber.

In embodiments, the sensor 126 further includes a photodetector 176 disposed to detect light 172 that transmits through the adhesion layer 164 and the bottom 162 of the collection chamber 154. The photodetector 176 can be a complementary metal-oxide-semiconductor (CMOS), such as the TSL 2591 light-to-digital converter distributed by AMS Ag (Premstraetten, Austria). In these embodiments, the sensor 126 provides output to the controller 92 that varies as a function of the volume of airborne particulate matter 150 collected at the adhesion layer 164 because the photodetector 176 provides output to the controller 92 that varies as a function of the volume of airborne particulate matter 150 collected at the adhesion layer 164. As the volume of the airborne particulate matter 150 trapped at the adhesion layer 164 within the collection chamber 154 increases, the amount of the light 172 transmitting from the light source 170 to the photodetector 176 decreases. The greater the volume of the airborne particulate matter 150 trapped at the adhesion layer 164, the greater the amount of light 172 that the airborne particulate matter 150 reflects or absorbs and the lesser the amount of light 172 that transmits to the photodetector 176. Thus, as the volume of airborne particulate matter 150 at the adhesion layer 164 increases, the output of the photodetector 176 changes (e.g., the current decreases). The graph of FIG. 15 illustrates this, with the output (electrical current I) changing as a function of time, specifically, the change in electrical current (ΔI) compared to baseline ($I_0$).

The collection chamber 154 can be fabricated from polymethyl methacrylate (PMMA) using a laser cutter. The bottom 162 can be fabricated to provide a base for the adhesion layer 164 and an optical window for the photodetector 176. A middle layer can be fabricated to provide the height 160 of the collection chamber 154. A top layer can be fabricated to provide the outlet 156 for the airflow 152 into the collection chamber 154, the exit 166 for the airflow 152 out of the collection chamber 154, and an optical window for light 172 from the light source 170 to transmit into the collection chamber 154. An example collection chamber 154 has a length 168 of 1.6 cm, a height 160 of 0.4 cm, and a width of 0.5 cm. An example of the adhesion layer 164 is 268L polystyrene adhesive (distributed by 3M, St. Paul, Minn., USA) applied to the bottom 162. The three layers of PMMA can be mechanically pressed to form a unitary body. An indium gallium nitride LED is an example of the light source 170. The light source 170 can be placed above the optical window of the top layer of the collection chamber 154. The photodetector 176 can be placed below the optical window of the bottom 162 of the collection chamber 154.

Figure 16:
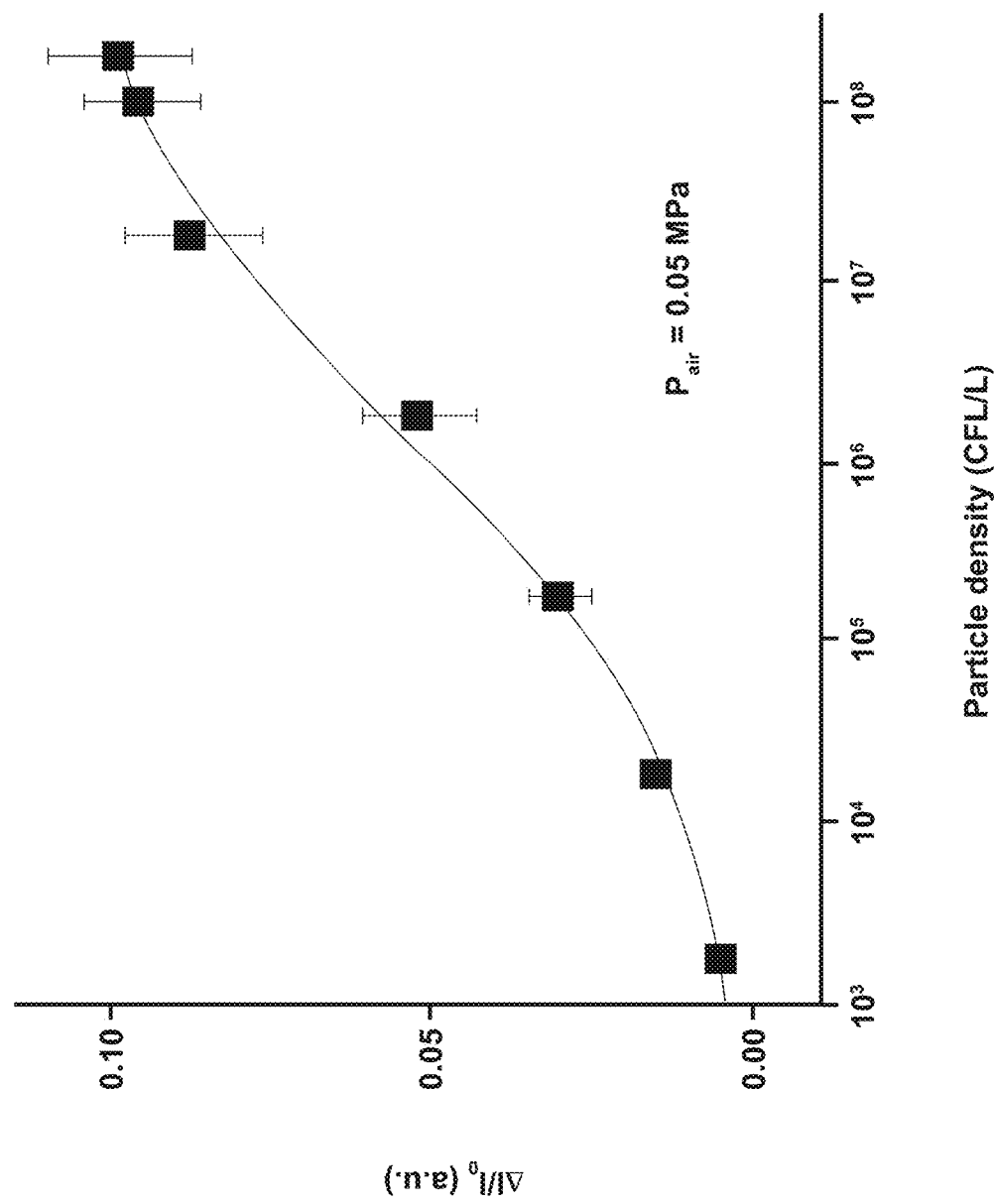
FIG. 16 is a graph of the ratio of the change in current to the baseline current of the photodetector of FIG. 13 as a function of the density of airborne particulate matter in the treatment chamber.

Differing densities of airborne particulate matter can lead to the photodetector 176 producing different changes in output (current I). The change in output thus can be calibrated and utilized to detect not only the presence of airborne particulate matter but the density of pathogens in the treatment chamber 54. The graphical results and a sample calibration curve are reproduced at FIG. 16.

In embodiments, the controller 92 activates the source of ultraviolet light 46 when the sensor 126 detects the presence of airborne particulate matter 150, and does not activate the source of ultraviolet light 46 when the sensor 126 does not detect the presence of airborne particulate matter 150. In embodiments, the controller 92 causes the source of ultraviolet light 46 to emit ultraviolet light 34 for the predetermined period of time and, upon conclusion of the predetermined period of time, deactivates the source of ultraviolet light 46. In embodiments, the controller 92 determines the period of time as a function of the output of the sensor 126. For example, if the output of the sensor 126 is the current generated by the photodetector 176, the controller 92 induces airflow 146 from the treatment chamber 54 to the sensor 126 for a set time (e.g., 60 seconds). The controller 92 determines the predetermined period of time that the source of ultraviolet light 46 is to be activated from the change in current generated by the photodetector 176—that is, the larger the change in current, the longer the predetermined period of time (because there is a larger amount of airborne particulate matter 150 including pathogens on the object 32). This measure helps ensure that the predetermined period of time that the source of ultraviolet light 46 emits ultraviolet light 34 is tailored to the volume of airborne particulate matter 150 on the object 32 placed in the treatment chamber 54, therefore optimizing energy expenditure.

In embodiments, the adhesion layer 164 is a biofilm with surface chemistry that covalently bonds specifically only to one or more pathogens or types of pathogens. For example, the surface chemistry bonds only to gram negative bacteria, or only *E. coli*, or only a particular virus, rather than all airborne particulate matter 150. That measure helps ensure that the predetermined period of time that the source of ultraviolet light 46 emits ultraviolet light 34 is being effectively utilized.

The sensor 126 has applications outside of the vehicle 10 and can be utilized to monitor air quality of any environment. In such applications, as well as in the vehicle 10, the sensor 126 can be in communication with a wireless communication device (e.g., a Bluetooth® device) to deliver output to an electronic device 122 of the passenger 42 or some other person. This allows for real-time analysis and detection of pathogens. In embodiments, the collection chamber 154 (whether including a biochip as the adhesion layer 164 or not) is replaced after each use.

In embodiments, the housing 44 further includes a wireless charging pad 178 within either the door 48 (above the barrier 76) or at the housing 44 (between the floor 52 and the platform 56). The wireless charging pad 178 uses electromagnetic induction to provide wireless power transfer. If the object 32 is capable of receiving wireless power transfer from the wireless charging pad 178, the passenger 42 can simultaneously treat the object 32 with ultraviolet light 34 and charge the object 32.

It is to be understood that variations and modifications can be made on the aforementioned structure without departing from the concepts of the present invention, and further it is to be understood that such concepts are intended to be covered by the following claims unless these claims by their language expressly state otherwise.

What is claimed is:

1. A treatment apparatus for a vehicle comprising:
a housing with at least one wall and a floor forming a treatment chamber;
a source of ultraviolet light configured to emit ultraviolet light into the treatment chamber;
a controller in communication with the source of ultraviolet light; and
a bandpass filter disposed between the source of the ultraviolet light and treatment chamber that transmits less than 10 percent of ultraviolet light having a wavelength of 290 nm to 400 nm but transmits greater than 10 percent of ultraviolet light having a wavelength of 240 nm to 280 nm;
wherein, the controller determines (i) a total energy that the source of ultraviolet light is to emit into the treatment chamber, and (ii) an intensity of ultraviolet light as a function of the total energy and a predetermined period of time; and
wherein, the controller causes the source of ultraviolet light to emit ultraviolet light for the predetermined period of time and at the intensity and, upon conclusion of the predetermined period of time, deactivates the source of ultraviolet light.

2. The treatment apparatus of claim 1 further comprising:
a door connected to the housing, the door having (i) an open position providing access to the treatment chamber and (ii) a closed position denying access to the treatment chamber and, together with the housing, preventing emitted ultraviolet light from irradiating beyond the treatment chamber.

3. The treatment apparatus of claim 2 further comprising:
a sensor that produces output that varies as a function of the door being in the open position or the closed position; and
wherein, the controller is in further communication with the sensor and deactivates the source of ultraviolet light when the sensor produces output indicative of the door being in the open position.

4. The treatment apparatus of claim 1 further comprising:
a display;
wherein, the controller is in further communication with the display and causes the display to provide a visual indication that the source of ultraviolet light is emitting ultraviolet light when the controller is causing the source of ultraviolet light to emit ultraviolet light.

5. The treatment apparatus of claim 2 further comprising:
a locking system that prevents the door from transitioning from the closed position to the open position while the source of ultraviolet light is emitting ultraviolet light.

6. A treatment apparatus for a vehicle comprising:
a housing with a wall and a floor forming a treatment chamber;
a source of ultraviolet light configured to emit ultraviolet light into the treatment chamber; and
a bandpass filter disposed between the source of ultraviolet light and the treatment chamber that transmits a greater percentage of ultraviolet light having a wavelength of 240 nm to 280 nm than ultraviolet light having a wavelength of 290 nm to 400 nm.

7. The treatment apparatus of claim 6 further comprising:
a coating disposed over a portion of the housing open to the treatment chamber that reflects at least 50 percent of ultraviolet light having a wavelength of 240 nm to 280 nm.

8. The treatment apparatus of claim 7 further comprising:
a door connected to the housing, the door having (i) an open position providing access to the treatment chamber and (ii) a closed position denying access to the treatment chamber;
wherein, the coating is further disposed over a portion of the door that is open to the treatment chamber.

9. The treatment apparatus of claim 6 further comprising:
a metal heatsink in thermal communication with the source of ultraviolet light.

10. The treatment apparatus of claim 6 further comprising:
a fan positioned to circulate air onto the source of ultraviolet light or a printed circuit board upon which the source of ultraviolet light is mounted.

11. The treatment apparatus of claim 6 further comprising:
a sensor in communication with a controller, the sensor producing output to the controller that varies as a function of a temperature of the source of ultraviolet light or a printed circuit board upon which the source of ultraviolet light is mounted, and the controller deactivates the source of ultraviolet light as a function of the output of the sensor.

12. A treatment apparatus for a vehicle comprising:
a housing with at least one wall and a floor forming a treatment chamber;
a source of ultraviolet light configured to emit ultraviolet light into the treatment chamber;
a sensor that collects a volume of airborne particulate matter and provides a signal that varies as a function of the volume of airborne particulate matter collected; and
a controller in communication with the source of ultraviolet light and the sensor that, as a function of the signal from the sensor, causes the source of ultraviolet light to emit ultraviolet light for a predetermined period of time and, upon conclusion of the predetermined period of time, deactivates the source of ultraviolet light.

13. The treatment apparatus of claim 6 further comprising:
a controller in communication with the source of ultraviolet light; and
a user interface in communication with the controller where a passenger of the vehicle inputs a predetermined period of time that the source of ultraviolet light is to emit ultraviolet light into the treatment chamber;
wherein, the controller causes the source of ultraviolet light to emit ultraviolet light for the predetermined period of time and, upon conclusion of the predetermined period of time, deactivates the source of ultraviolet light.

14. The treatment apparatus of claim 6 further comprising:
a controller in communication with the source of ultraviolet light; and
a user interface in communication with the controller, the user interface providing selectable options for identifying an object to be treated in the treatment chamber for a passenger of the vehicle to select as a selected option of the selectable options;
wherein, the controller causes the source of ultraviolet light to emit ultraviolet light for a predetermined period of time and, upon conclusion of the predetermined period of time, deactivates the source of ultraviolet light; and
wherein, the controller determines the predetermined period of time as a function of the selected option.

15. The treatment apparatus of claim 6 further comprising:
a controller in communication with the source of ultraviolet light; and
a camera in communication with the controller that captures an image of an object to be treated in the treatment chamber;
wherein, the controller causes the source of ultraviolet light to emit ultraviolet light for a predetermined period of time and, upon conclusion of the predetermined period of time, deactivates the source of ultraviolet light; and
wherein, the controller determines the predetermined period of time as a function of the image of the object.

16. The treatment apparatus of claim 12, wherein
the sensor comprises an adhesion layer where the volume of airborne particulate matter is collected, a light source directing light to a first side of the adhesion layer, and a photodetector disposed on a second side of the adhesion layer; and
the photodetector provides output that varies as a function of the volume of airborne particulate matter collected at the adhesion layer.

17. The treatment apparatus of claim 16, wherein
a first airflow to a junction causes a second airflow from the treatment chamber to flow to the junction and combine into combined airflow, and the combined airflow of the first airflow and the second airflow directs the volume of airborne particulate matter to a collection chamber that includes the adhesion layer.

18. The treatment apparatus of claim 2, wherein
the source of ultraviolet light does not emit ultraviolet light if the door is in the open position.

19. The treatment apparatus of claim 1 further comprising:
a coating disposed over a portion of the housing open to the treatment chamber that reflects at least 50 percent of ultraviolet light having a wavelength of 240 nm to 280 nm.

* * * * *

UNITED STATES PATENT AND TRADEMARK OFFICE
CERTIFICATE OF CORRECTION

| | |
|---|---|
| PATENT NO. | : 11,865,234 B2 |
| APPLICATION NO. | : 16/837653 |
| DATED | : January 9, 2024 |
| INVENTOR(S) | : Chen et al. |

It is certified that error appears in the above-identified patent and that said Letters Patent is hereby corrected as shown below:

In the Claims

Column 17:
Claim 1, Line 10;
After "and" insert --the--.

Signed and Sealed this
Twelfth Day of March, 2024

Katherine Kelly Vidal
*Director of the United States Patent and Trademark Office*